(12) United States Patent
Taguchi et al.

(10) Patent No.: US 8,519,223 B2
(45) Date of Patent: Aug. 27, 2013

(54) **MARKER FOR SELECTING AN *APHANOMYCES COCHLIOIDES*-RESISTANT VARIETY AND SELECTION METHOD THEREFOR**

(75) Inventors: Kazunori Taguchi, Kasai-gun (JP); Naoki Oogata, Edogawa-ku (JP); Kazuyuki Okazaki, Kasai-gun (JP); Keiji Nakatsuka, Kasai-gun (JP); Hiroyuki Takahashi, Kasai-gun (JP)

(73) Assignee: National Agriculture and Food Research Organization, Tsukuba-shi (JP)

( * ) Notice: Subject to any disclaimer, the term of this patent is extended or adjusted under 35 U.S.C. 154(b) by 884 days.

(21) Appl. No.: 12/226,813

(22) PCT Filed: Apr. 25, 2007

(86) PCT No.: PCT/JP2007/058952
§ 371 (c)(1),
(2), (4) Date: Jan. 26, 2009

(87) PCT Pub. No.: WO2007/125958
PCT Pub. Date: Nov. 8, 2007

(65) Prior Publication Data
US 2009/0222941 A1    Sep. 3, 2009

(30) Foreign Application Priority Data
Apr. 28, 2006  (JP) ................. 2006-126570

(51) Int. Cl.
*A01H 5/00* (2006.01)
*A01H 1/00* (2006.01)
*C12N 15/11* (2006.01)
*C12N 15/82* (2006.01)
*C12Q 1/68* (2006.01)

(52) U.S. Cl.
USPC .......... 800/279; 800/298; 800/301; 800/265; 800/266; 800/267; 435/6.11

(58) Field of Classification Search
None
See application file for complete search history.

(56) References Cited

FOREIGN PATENT DOCUMENTS
JP    2004-321055    11/2004

OTHER PUBLICATIONS

Kazunori Taguchi et al, "Quantitative trait locus responsible for resistance to *Aphanomyces* root rot (black root) caused by *Aphanomyces cochlioides* Drechs. in sugar beet", Theoretical and Applied Genetics, International Journal of Plant Breeding Research, vol. 118, No. 2, Sep. 24, 2008, pp. 227-234.
Suren Samuelian et al, "Cloning and functional analyses of a gene from sugar beet up-regulated upon cyst nematode infection", Plant Molecular Biology, vol. 54, No. 1, Jan. 1, 2004, pp. 147-156.
Pilet-Nayel M L et al, "Consistent Quantitative Trait Loci in Pea for Partial Resistance to *Aphanomyces euteiches* Isolates from the United States and France.", Phytopathology, vol. 95, No. 11, Nov. 2005, pp. 1287-1293.
Kazunori Taguchi et al, Construction of linkage map of *Beta vulgaris* L. based on AFLP and RAPD, The Crop Science Society of Japan 44, 2003, 83-84 pp, Japan.
Kazunori Taguchi et al, Breeding of *Aphanomyces cochlioided*-resistant variety of *Beta vulgaris* L Genetic effect of 'NK-310mm-0', The Crop Science Society of Japan 45, 2003, 43-44 pp, Japan.
Tsutomu Kajiyama et al, Effects of *Aphanomyces* Root Rot on the Yield and Qualities of Sugar Beet, Proc. Japan Soc. Sugar Beet Technol. 41, 2000, 59-64 pp, Japan.
Kazunori Taguchi et al, Breeding *Aphanomyces* Root Rot Resistance in Sugar Beet, Proc. Japan Soc. Sugar Beet Technol. 43, 2001, 36-43 pp, Japan.
P. Vos, et al., AFLP: a new technique for DNA fingerprinting, Nucleic Acids Research, 1995, vol. 23, No. 21, pp. 4407-4414.

*Primary Examiner* — Medina A Ibrahim
(74) *Attorney, Agent, or Firm* — Fox Rothschild LLP

(57) ABSTRACT

As an effective means of controlling *Aphanomyce cochlioides*, to provide a method of highly accurately selecting an *Aphanomyce cochlioides*-resistant plant variety by using a molecular biological method without depending on the phenotype. To efficiently grow the resultant *Aphanomyce cochlioides*-resistant plant variety. A method of selecting an *Aphanomyce cochlioides*-resistant plant variety based on the AFLP method with the use of primers for selecting an *Aphanomyce cochlioides*-resistant plant variety which strongly link with the locus of an allele having the dominant phenotype of the resistance against *Aphanomyce cochlioides*.

9 Claims, 7 Drawing Sheets

Fig. 1
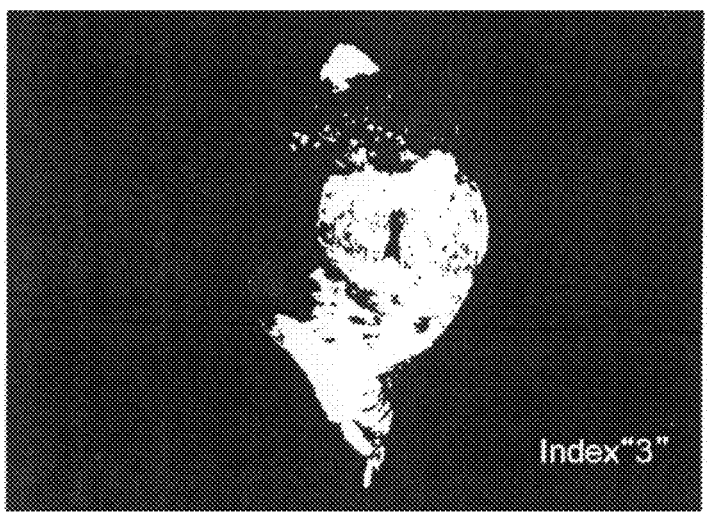
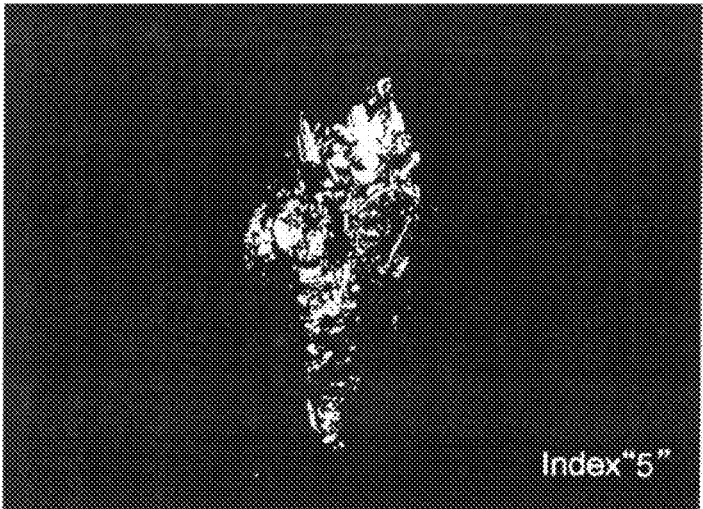

Fig.2
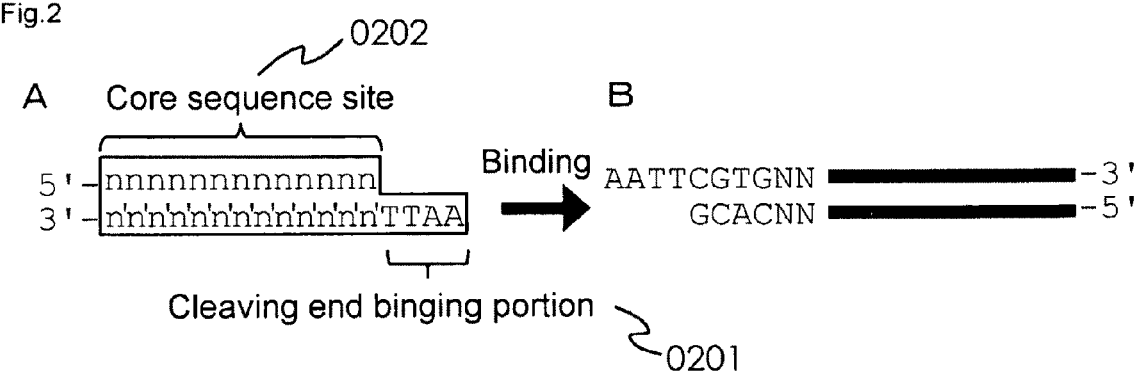
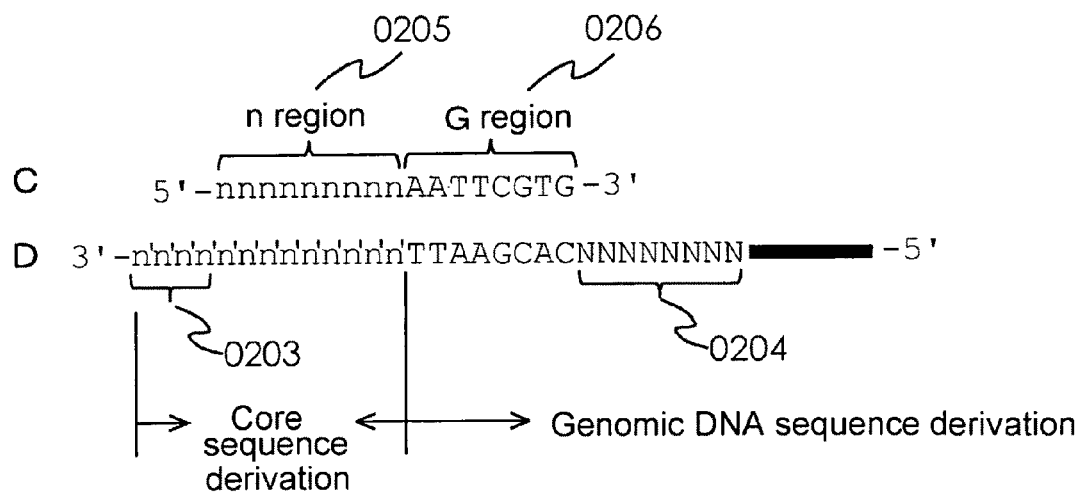

SEQUENCE LISTING

```
<160> NUMBER OF SEQ ID NOS: 17

<210> SEQ ID NO 1
<211> LENGTH: 17
<212> TYPE: DNA
<213> ORGANISM: Beta vulgaris
<220> FEATURE:
<221> NAME/KEY: primer_bind
<222> LOCATION: (10)..(17)
<223> OTHER INFORMATION:
<220> FEATURE:
<221> NAME/KEY: misc_feature
<222> LOCATION: (1)..(9)
<223> OTHER INFORMATION: "n" in a sequence may be any one of A, T, G, or
      C. Note that, a sequence consisted of "n" is preferably a
      complement sequence to an adaptor sequence used in AFLP method.

<400> SEQUENCE: 1
nnnnnnnnna attcgtg                                                  17

<210> SEQ ID NO 2
<211> LENGTH: 17
<212> TYPE: DNA
<213> ORGANISM: Beta vulgaris
<220> FEATURE:
<221> NAME/KEY: misc_feature
<222> LOCATION: (1)..(11)
<223> OTHER INFORMATION: "n" in a sequence may be any one of A, T, G, or
      C. Note that, a sequence consisted of "n" is preferably a
      complement sequence to an core sequence of adaptor used in AFLP
      method.
<220> FEATURE:
<221> NAME/KEY: primer_bind
```

```
<222> LOCATION: (12)..(17)
<223> OTHER INFORMATION:

<400> SEQUENCE: 2
nnnnnnnnnn ntaagcg                                                17

<210> SEQ ID NO 3
<211> LENGTH: 17
<212> TYPE: DNA
<213> ORGANISM: Beta vulgaris
<220> FEATURE:
<221> NAME/KEY: misc_feature
<222> LOCATION: (1)..(9)
<223> OTHER INFORMATION: "n" in a sequence may be any one of A, T, G, or
      C. Note that, a sequence consisted of "n" is preferably a
      complement sequence to an core sequence of adaptor used in AFLP
      method.
<220> FEATURE:
<221> NAME/KEY: primer_bind
<222> LOCATION: (10)..(17)
<223> OTHER INFORMATION:

<400> SEQUENCE: 3
nnnnnnnnna attcaag                                                17

<210> SEQ ID NO 4
<211> LENGTH: 17
<212> TYPE: DNA
<213> ORGANISM: Beta vulgaris
<220> FEATURE:
<221> NAME/KEY: misc_feature
<222> LOCATION: (1)..(11)
<223> OTHER INFORMATION: "n" in a sequence may be any one of A, T, G, or
      C. Note that, a sequence consisted of "n" is preferably a
      complement sequence to an core sequence of adaptor used in AFLP
      method.
<220> FEATURE:
<221> NAME/KEY: primer_bind
<222> LOCATION: (12)..(17)
<223> OTHER INFORMATION:

<400> SEQUENCE: 4
nnnnnnnnnn ntaaccg                                                17

<210> SEQ ID NO 5
<211> LENGTH: 17
<212> TYPE: DNA
<213> ORGANISM: Beta vulgaris
<220> FEATURE:
<221> NAME/KEY: misc_feature
<222> LOCATION: (1)..(11)
<223> OTHER INFORMATION: "n" in a sequence may be any one of A, T, G, or
      C. Note that, a sequence consisted of "n" is preferably a
      complement sequence to an core sequence of adaptor used in AFLP
      method.
<220> FEATURE:
<221> NAME/KEY: primer_bind
<222> LOCATION: (12)..(17)
<223> OTHER INFORMATION:

<400> SEQUENCE: 5
nnnnnnnnnn ntaacgg                                                17

<210> SEQ ID NO 6
<211> LENGTH: 135
<212> TYPE: DNA
<213> ORGANISM: Beta vulgaris
<220> FEATURE:
<221> NAME/KEY: misc_feature
<222> LOCATION: (1)..(135)
<223> OTHER INFORMATION: This sequence is linked to a gene involved in
      Aphanomyces root rot resistance on the genome sequence.
```

```
<400> SEQUENCE: 6
taagcgaaga attacaataa aaaacataaa ttacgaagtg taattgttac accataaact      60
accacctcta ggagatttat gtaggagccc aatggttgga gctcccacct cccaacctca     120
tactggttag gaatt                                                      135

<210> SEQ ID NO 7
<211> LENGTH: 172
<212> TYPE: DNA
<213> ORGANISM: Beta vulgaris
<220> FEATURE:
<221> NAME/KEY: misc_feature
<222> LOCATION: (1)..(172)
<223> OTHER INFORMATION: "n"s in a sequence are unkown bases. This
      sequence is linked to a gene involved in Aphanomyces root rot
      resistance on the genome sequence.

<400> SEQUENCE: 7
taagccgaag ccacncntac tnactnactn gcattttcca tctttctcca aatctttgtc      60
ctctccncnt ncncnntntc ccntgtgatt cagaggccan natcgcttga aactagtaat     120
ggtgggcttt tgnnaattgc tcccattgaa aaccagaatt ttgccttgaa tt             172

<210> SEQ ID NO 8
<211> LENGTH: 307
<212> TYPE: DNA
<213> ORGANISM: Beta vulgaris
<220> FEATURE:
<221> NAME/KEY: misc_feature
<222> LOCATION: (1)..(307)
<223> OTHER INFORMATION: This sequence is linked to a gene involved in
      Aphanomyces root rot resistance on the genome sequence.

<400> SEQUENCE: 8
taacgggtcg ttttagggtt gcatattgtt caaggtccgg ttcaaggtta gggctaagtc      60
gatttcctca tccatcaatt tagaatatga gaacccattt gattctgcgg atccagaccg     120
gttcaagcct tgtcgtctgg cgattcagat cgagccggtc ttcttgcggg tcgattcaag     180
gttgtgtcca aggatccccg cccaatgaac caagttttag tactaaactg tcaataattt     240
ttcccataaa aacaaaaata aaccctaatc atcattcttt atgaaataga ttatggagcc     300
ttgaatt                                                               307

<210> SEQ ID NO 9
<211> LENGTH: 17
<212> TYPE: DNA
<213> ORGANISM: Beta vulgaris
<220> FEATURE:
<221> NAME/KEY: misc_feature
<222> LOCATION: (1)..(17)
<223> OTHER INFORMATION: This sequence is a primer sequence for pre-
      amplification in AFLP method.
<300> PUBLICATION INFORMATION:
<301> AUTHORS: Vos P., Hoger R., Bleeker M., Reijans M., Lee T.V.D.,
      Hornes M., Frijters A., Pot J., Peleman J., Kuiper M. and
      Zabeau M.
<302> TITLE: AFLP: a new technique for DNA fingerprinting
<303> JOURNAL: Nucleic Acids Research
<304> VOLUME: 23
<305> ISSUE: 21
<306> PAGES: 8
<307> DATE: 1995-11-11
<309> DATABASE ENTRY DATE:
<313> RELEVANT RESIDUES IN SEQ ID NO: (4407)..(4414)

<400> SEQUENCE: 9
gactgcgtac caattcg                                                     17
```

```
<210> SEQ ID NO 10
<211> LENGTH: 17
<212> TYPE: DNA
<213> ORGANISM: Beta vulgaris
<220> FEATURE:
<221> NAME/KEY: misc_feature
<222> LOCATION: (1)..(17)
<223> OTHER INFORMATION: This sequence is a primer sequence for pre-
      amplification in AFLP method.
<300> PUBLICATION INFORMATION:
<301> AUTHORS: Vos P., Hoger R., Bleeker M., Reijans M., Lee T.V.D.,
      Hornes M., Frijters A., Pot J., Peleman J., Kuiper M. and
      Zabeau M.
<302> TITLE: AFLP: a new technique for DNA fingerprinting
<303> JOURNAL: Nucleic Acids Research
<304> VOLUME: 23
<305> ISSUE: 21
<306> PAGES: 8
<307> DATE: 1995-11-11
<309> DATABASE ENTRY DATE:
<313> RELEVANT RESIDUES IN SEQ ID NO: (4407)..(4414)

<400> SEQUENCE: 10
gatgagtcct gagtaag                                                17

<210> SEQ ID NO 11
<211> LENGTH: 17
<212> TYPE: DNA
<213> ORGANISM: Beta vulgaris
<220> FEATURE:
<221> NAME/KEY: misc_feature
<222> LOCATION: (1)..(17)
<223> OTHER INFORMATION: This sequence is a primer sequence for pre-
      amplification in AFLP method.
<300> PUBLICATION INFORMATION:
<301> AUTHORS: Vos P., Hoger R., Bleeker M., Reijans M., Lee T.V.D.,
      Hornes M., Frijters A., Pot J., Peleman J., Kuiper M. and
      Zabeau M.
<302> TITLE: AFLP: a new technique for DNA fingerprinting
<303> JOURNAL: Nucleic Acids Research
<304> VOLUME: 23
<305> ISSUE: 21
<306> PAGES: 8
<307> DATE: 1995-11-11
<309> DATABASE ENTRY DATE:
<313> RELEVANT RESIDUES IN SEQ ID NO: (4407)..(4414)

<400> SEQUENCE: 11
gactgcgtac caattca                                                17

<210> SEQ ID NO 12
<211> LENGTH: 17
<212> TYPE: DNA
<213> ORGANISM: Beta vulgaris
<220> FEATURE:
<221> NAME/KEY: misc_feature
<222> LOCATION: (1)..(17)
<223> OTHER INFORMATION: This sequence is a primer sequence for pre-
      amplification in AFLP method.
<300> PUBLICATION INFORMATION:
<301> AUTHORS: Vos P., Hoger R., Bleeker M., Reijans M., Lee T.V.D.,
      Hornes M., Frijters A., Pot J., Peleman J., Kuiper M. and
      Zabeau M.
<302> TITLE: AFLP: a new technique for DNA fingerprinting
<303> JOURNAL: Nucleic Acids Research
<304> VOLUME: 23
<305> ISSUE: 21
<306> PAGES: 8
<307> DATE: 1995-11-11
<309> DATABASE ENTRY DATE:
<313> RELEVANT RESIDUES IN SEQ ID NO: (4407)..(4414)

<400> SEQUENCE: 12
```
gatgagtcct gagtaac                                                          17

<210> SEQ ID NO 13
<211> LENGTH: 19
<212> TYPE: DNA
<213> ORGANISM: Beta vulgaris
<220> FEATURE:
<221> NAME/KEY: misc_feature
<222> LOCATION: (1)..(11)
<223> OTHER INFORMATION: This sequence is complementaly to core sequence
      of adaptor used in AFLP method.
<220> FEATURE:
<221> NAME/KEY: primer_bind
<222> LOCATION: (12)..(19)
<223> OTHER INFORMATION:

<400> SEQUENCE: 13
gactgcgtac caattcgtg                                                        19

<210> SEQ ID NO 14
<211> LENGTH: 19
<212> TYPE: DNA
<213> ORGANISM: Beta vulgaris
<220> FEATURE:
<221> NAME/KEY: misc_feature
<222> LOCATION: (1)..(13)
<223> OTHER INFORMATION: This sequence is complementaly to core sequence
      of adaptor used in AFLP method.
<220> FEATURE:
<221> NAME/KEY: primer_bind
<222> LOCATION: (14)..(19)
<223> OTHER INFORMATION:

<400> SEQUENCE: 14
gatgagtcct gagtaagcg                                                        19

<210> SEQ ID NO 15
<211> LENGTH: 19
<212> TYPE: DNA
<213> ORGANISM: Beta vulgaris
<220> FEATURE:
<221> NAME/KEY: misc_feature
<222> LOCATION: (1)..(11)
<223> OTHER INFORMATION: This sequence is complementaly to core sequence
      of adaptor used in AFLP method.
<220> FEATURE:
<221> NAME/KEY: primer_bind
<222> LOCATION: (12)..(19)
<223> OTHER INFORMATION:

<400> SEQUENCE: 15
gactgcgtac caattcaag                                                        19

<210> SEQ ID NO 16
<211> LENGTH: 19
<212> TYPE: DNA
<213> ORGANISM: Beta vulgaris
<220> FEATURE:
<221> NAME/KEY: misc_feature
<222> LOCATION: (1)..(13)
<223> OTHER INFORMATION: This sequence is complementaly to core sequence
      of adaptor used in AFLP method.
<220> FEATURE:
<221> NAME/KEY: primer_bind
<222> LOCATION: (14)..(19)
<223> OTHER INFORMATION:

<400> SEQUENCE: 16
gatgagtcct gagtaaccg                                                        19

<210> SEQ ID NO 17

-continued

```
<211> LENGTH: 19
<212> TYPE: DNA
<213> ORGANISM: Beta vulgaris
<220> FEATURE:
<221> NAME/KEY: primer_bind
<222> LOCATION: (14)..(19)
<223> OTHER INFORMATION:
<220> FEATURE:
<221> NAME/KEY: misc_feature
<222> LOCATION: (1)..(13)
<223> OTHER INFORMATION: This sequence is complementaly to core sequence
      of adaptor used in AFLP method.

<400> SEQUENCE: 17
gatgagtcct gagtaacgg                                                    19
```

MARKER FOR SELECTING AN *APHANOMYCES COCHLIOIDES*-RESISTANT VARIETY AND SELECTION METHOD THEREFOR

BACKGROUND OF THE INVENTION

1. Field of the Invention

The present invention relates to a primer as a marker for selecting an *Aphanomyce cochlioides*-resistant plant variety and a selection method therefor, an *Aphanomyce cochlioides*-resistant variety acquired through the aforementioned method, and a methodology for identifying an *Aphanomyce cochlioides*-resistant gene.

2. Description of the Related Art

The *Aphanomyce cochlioides* are developed through a type of soil-borne fungus that infects plants of the *Beta* genus, such as *Beta vulgaris* L., etc. as crops for sugar manufacture. It is difficult to prevent and eliminate such damage. Major disease characteristics thereof include damping-off disease of seedlings in which seedlings die in an upright position during the seedling stages, and root rot symptoms in which humid black spots as shown in FIG. 1 appear in a root section during a later growth stage and rot is caused thereto (non-patent document 1). Major damage includes reduction of crop yields of *Beta vulgaris* L. at the point of production thereof and the infecting of *Beta vulgaris* L. by affected *Beta vulgaris* L. within piles, etc. Furthermore, disease damage extends to mixtures including rotten roots in the sugar manufacturing process and reduction of sugar yields in the sugar manufacturing industry. All such damages have become major issues (non-patent document 2).

Methods of control of such disease have been studied in the U.S.A, Japan, and Europe. However, no effective method has yet been found. For instance, the improvement of water permeability and drainage of agricultural fields of *Beta vulgaris* L., the search for active medical agents, and the selection of resistant plant variety have been reviewed. However, in relation to improvement of water permeability and drainage of agricultural fields, huge investments upon undertaking of construction may be necessary, which would make it difficult to realize the same. Additionally, in relation to control based on medical agents, there are no specifically effective agents at present. Furthermore, it is problematic that the root portion is a diseased area resulting from the disease, and therefore, medical agents are not sufficiently able to circulate therein. Selection of a resistant plant variety would seem to be the most effective measure for controlling such disease. However, a method for selection of a resistant plant variety based on the conventional art depends on root phenotypic disease symptoms. Therefore, problems have been caused when affected stocks that did not show accidental disease symptoms due to influence of environmental factors, etc., have been wrongly judged as resistant stocks, and selection also requires enormous efforts, time, and costs.

The *Beta vulgaris* L. market is enormous, exceeding 860,000,000,000 yen per year throughout the world. *Aphanomyce cochlioides* could have a great influence on crop yields of *Beta vulgaris* L., and by extension, could have a major influence on the supply amounts of raw materials for sugar manufacturing. Thus, the impact on the market is immeasurable. Accordingly, in the breeding industry in Europe, breeding of an *Aphanomyce cochlioides*-resistant plant variety is an object of focus, and this involves spending enormous costs, time, and efforts, even at present. However, it has been impossible to obtain effective study outcomes regarding *Aphanomyce cochlioides*-resistant varieties and *Aphanomyce cochlioides*-resistant genes to date.

Non-patent document 1: Tsutomu Kajiyama and Fumio Tanaka, proceedings of Japanese Society of Sugar Beet Technologists, 2000, 42:59-63.

Non-patent document 2: Kazunori Taguchi, Naoki Oogata, and Masakatsu Tanaka, proceedings of Japanese Society of Sugar Beet Technologists, 2001, 43:36-43.

Non-patent document 3: Vos P, et al., Nucleic Acid Res., 1995, 23:4407-4414

SUMMARY OF THE INVENTION

Problems to be Solved by the Invention

The objectives of the present invention include the development of an effective measure method in regards to *Aphanomyce cochlioides* and the prevention of reduction of sugar yields through such method, in light of the issues mentioned above. Therefore, the first purpose of the invention of the present application is to discover a plant variety with resistance against *Aphanomyce cochlioides* and to supply a method for selection of such plant variety with a high degree of accuracy via a molecular biological technique that does not depend upon phenotype. Additionally, the second purpose of the invention of the present application is to efficiently foster an *Aphanomyce cochlioides*-resistant plant variety via the method mentioned above. Furthermore, the third purpose of the invention of the present application is to supply a methodology for identifying a gene with resistance against *Aphanomyce cochlioides*.

Means for Solving the Problems

In order to resolve the aforementioned issues, as a result of repeated and earnest studies, the present inventor discovered a plant variety with high resistance against *Aphanomyce cochlioides*. Furthermore, based on a DNA polymorphism using the AFLP method ("the AFLP method" is a registered trademark) and genetic analysis, the present inventor was successful in developing a primer for selecting an *Aphanomyce cochlioides*-resistant plant variety that is strongly linked with the locus of an allele in which resistance against *Aphanomyce cochlioides* corresponds to a dominant phenotype, and in developing a method for selection of an *Aphanomyce cochlioides*-resistant plant variety using the same. The inventions shown in (1) through (5) as below have been completed based on the aforementioned discoveries by the present inventors and others, and are supplied as a means for solving the problems mentioned above.

(1) The present invention provides primers for selecting an *Aphanomyce cochlioides*-resistant plant variety composed of any one of the base sequences of SEQ ID NOs: 1 through 5.

(2) The present invention provides base sequences represented by any one of SEQ ID NOs: 6 through 8, or polynucleotides that are composed of base sequences having homology of 90% or more with base sequences represented by any one of SEQ ID NOs: 6 through 8. Additionally, the present invention provides seeds having resistance against the *Aphanomyce cochlioides* and progenies of the *Aphanomyce cochlioides*-resistant plant variety comprising any one or more of such polynucleotides.

(3) The present invention provides a method for selecting an *Aphanomyce cochlioides*-resistant plant variety comprising the steps of extracting DNA from tissues of genus *Beta*, including *Beta vulgaris* L., based on the AFLP method, cleaving the extracted DNA using a restriction enzyme, amplifying nucleic acids as pairs of the primers according to (1) mentioned above based on the genomic DNA acquired in the aforementioned step of DNA cleaving to be used as a mold, and detecting polynucleotides that contain the base sequences according to (2) mentioned above which correspond to the primer pairs used for nucleic acid amplification from among the nucleic acids amplified in the step of amplifying nucleic acids mentioned above.

(4) The present invention provides the *Aphanomyce cochlioides*-resistant plant variety of genus *Beta* selected via the method for selecting an *Aphanomyce cochlioides*-resistant plant variety according to (3) mentioned above, seeds having resistance against the *Aphanomyce cochlioides*, and progenies of the *Aphanomyce cochlioides*-resistant plant variety of genus *Beta* produced through hybridization or cloning using the *Aphanomyce cochlioides*-resistant plant variety, and method for producing thereof.

(5) The present invention provides a methodology for identification of an *Aphanomyce cochlioides*-resistant gene, which identifies an *Aphanomyce cochlioides*-resistant gene using base sequence loci having base sequences according to (2) mentioned above and the fact that the genetic distance between the aforementioned base sequence loci having base sequences and the gene locus of such *Aphanomyce cochlioides*-resistant gene is about 2.2 cM on the genomic DNA of genus *Beta*, in particular third-chromosome DNA of *Beta vulgaris* L.

Advantageous Effect of the Invention

According to the method for selecting an *Aphanomyce cochlioides*-resistant plant variety of the present invention, it is possible to indirectly select a plant variety that shows resistance against *Aphanomyce cochlioides* based on a molecular biological method and not depending upon phenotype in a high accuracy manner.

Additionally, the method for selecting an *Aphanomyce cochlioides*-resistant plant variety of the present invention efficiently allows breeding of an *Aphanomyce cochlioides*-resistant plant variety without the necessity of enormous effort, time, or costs. With such *Aphanomyce cochlioides*-resistant plant variety, stable amounts of sugar yields can be preserved in the face of such illness. Thus, effectiveness of such method is highly expected at the market of *Beta vulgaris* L. And it is expected that such method will be used throughout the world. Moreover, the ripple effect caused thereby would be remarkably large, such as the beneficial influence expected in the sugar manufacturing industry and the like.

Furthermore, according to the methodology for identification of an *Aphanomyce cochlioides*-resistant gene of the present invention, the *Aphanomyce cochlioides*-resistant gene of genus *Beta* that is linked with the primer for selecting the *Aphanomyce cochlioides*-resistant plant variety mentioned above can be identified.

BRIEF DESCRIPTION OF DRAWINGS

FIG. 1 is an explanatory figure of root rot symptom as an *Aphanomyces cochlioides* disease symptom. A shows a strain that corresponds to a disease index "0" in which disease symptoms are not recognized (normal strain). B shows a strain that corresponds to a disease index "3" in which lesions accompanying internal rot are recognized. And C shows a strain that corresponds to a disease index "5" in which disease symptoms accompanying internal rot extending to the entire strain or death applies.

FIG. 2 is an explanatory figure for an adapter configuration and a configuration of the primer for selecting an *Aphanomyces cochlioides*-resistant plant variety bound therewith. A shows the EcoRI adapter, B shows the EcoRI cleaving end of a genomic DNA fragment, C shows the primer for selecting an *Aphanomyces cochlioides*-resistant plant variety (equivalent to the primer of claim 1), and D shows the mold genomic DNA which is bound with the adapter. In addition, the letter "n'" refers to the complementary base to "n" and the letter "N" refers to the base sequence on the genomic DNA.

Figure 5:
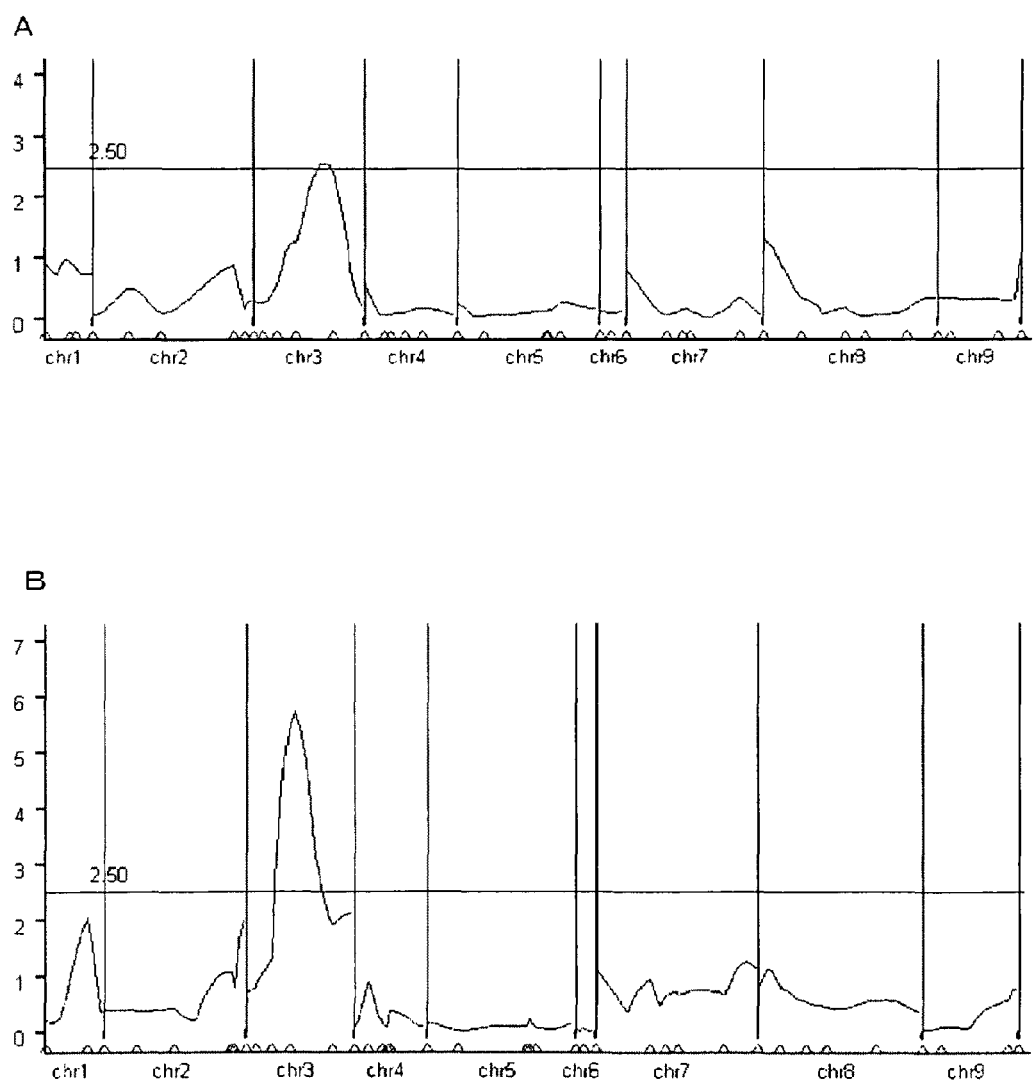

A of FIG. 5 is a figure that shows QTL analysis results for a disease index of *Aphanomyces cochlioides* classified by individual of F2 population of *Beta vulgaris* L. Additionally, B of FIG. 5 is a figure that shows QTL analysis result related to a disease index concerning *Aphanomyces cochlioides* of the F3 lines classified based on individuals of the F2 population of *Beta vulgaris* L. The expression "chr" on the horizontal axis refers to chromosomes, and the numbers refer to chromosome numbers in all figures. The vertical axis shows the logarithm of odds regarding the possibility of existence concerning a QTL location.

Figure 6:
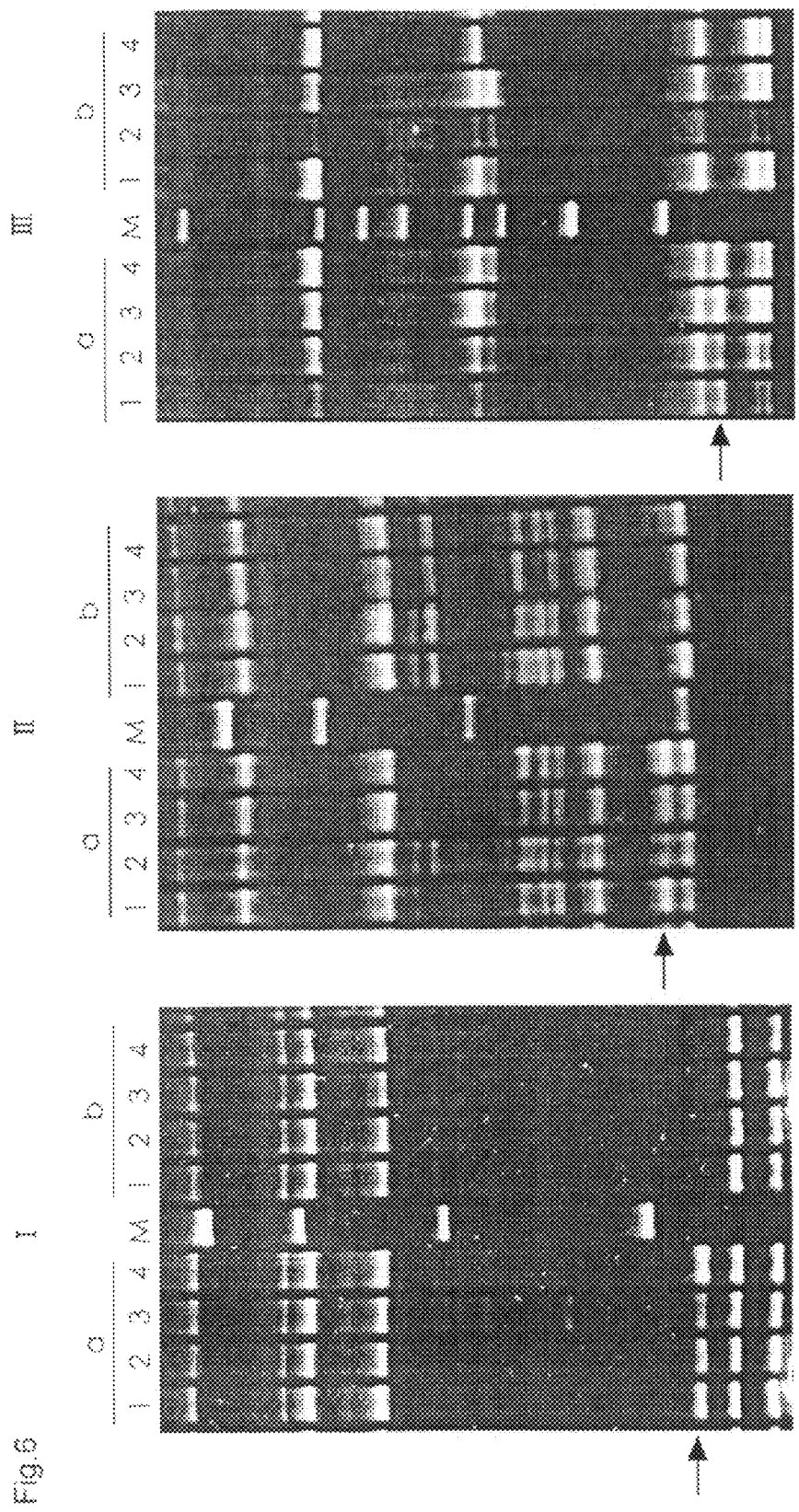
Figure 7:
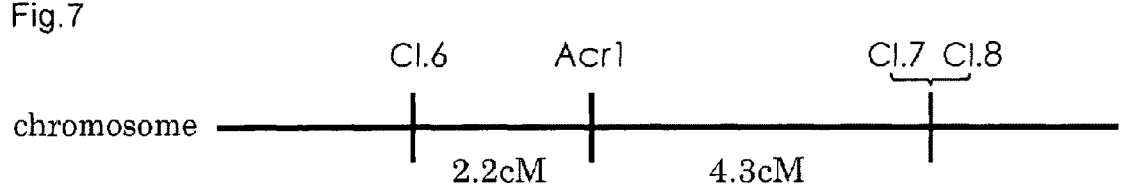

FIG. 6 is a figure relating to the result of selecting an *Aphanomyces cochlioides*-resistant plant variety via the method for selecting an *Aphanomyces cochlioides*-resistant plant variety of the first embodiment FIG. 7 is a linkage map relating to Acr1 as an *Aphanomyces cochlioides*-resistant gene and the base sequence loci having the base sequences according to claims 6 through 8. Cl. 6, Cl. 7, and Cl. 8 in the figure respectively show the base sequence loci having the base sequences according to claims 6, 7, and 8.

DETAILED DESCRIPTION OF THE PREFERRED EMBODIMENTS

The preferred embodiments for implementing all of the present inventions mentioned above are explained hereinafter. The present invention is not limited by such embodiments. That is to say, the present invention can be implemented in various forms without deviating from the main purposes thereof. A first embodiment mainly relates to claims 1 and 18. And a second embodiment mainly relates to claims 19 and 23.

First Embodiment

Outline of First Embodiment

The first embodiment relates to the invention related to the method for selecting an *Aphanomyce cochlioides*-resistant plant variety and an *Aphanomyce cochlioides*-resistant plant variety acquired via such method.

The present inventors conducted a study related to genetic resources having resistance against such illness based upon the *Aphanomyce cochlioides*-resistant plant variety discovered by the present inventors As a result, the present inventors were successful in developing three primer pairs that were strongly linked with the locus of allele associated with resistance against *Aphanomyce cochlioides*. It is possible to select an *Aphanomyce cochlioides*-resistant plant variety of the

First Embodiment

Configuration

The first embodiment comprises the primer for selecting an *Aphanomyce cochlioides*-resistant plant variety, polypeptides, the method for selecting an *Aphanomyce cochlioides*-resistant plant variety, and an *Aphanomyce cochlioides*-resistant plant variety acquired via the aforementioned method. Explanations in relation to the configuration of the present embodiment are specifically given hereinafter.

(Configuration of the Primer for Selecting an *Aphanomyce Cochlioides*-Resistant Plant Variety)

The term "primer for selecting the *Aphanomyce cochlioides*-resistant plant variety" refers to an oligonucleotide that comprises the base sequence represented by any one of base sequences of SEQ ID NOs: 1 through 5 that functions as a DNA marker used to detect the *Aphanomyce cochlioides*-resistant plant variety via the method for selecting an *Aphanomyce cochlioides*-resistant plant variety as described below. All primers mentioned above have base sequences that are linked with the *Aphanomyce cochlioides*-resistant genes as stated below on the genomes. The base sequences of the primers represented by SEQ ID NOs: 1 and 2 are about 2.2 cM (centi-morgans). And the base sequences related to the primers represented by SEQ ID NOs: 3 through 5 are about 4.3 cM (centi-morgans). Such base sequences are both located at a distance from the *Aphanomyce cochlioides*-resistant genes on the genomes.

Configuration of the primer for selecting the *Aphanomyce cochlioides*-resistant plant variety is explained with reference to FIG. 2. In regards to the base sequences represented by any one of SEQ ID NOs: 1 through 5, the base sequences represented by "n" (hereinafter referred to as "n region") are configured so as to be hybridized in a part of the adapter. For instance, as shown in FIG. 2C, when the primer for selection of the *Aphanomyce cochlioides*-resistant plant variety is represented by SEQ ID: 1, the n region (0205) has complementary base sequences with some or all of the base sequences of the adapter's core sequence sites as stated below. Additionally, in regards to the base sequences represented by any one of SEQ ID NOs: 1 through 5, any base sequences represented by base sequences other than "n" (hereinafter referred to as "G region(s) (0206)") comprise base sequences existing on the genomic DNA of *Beta vulgaris* L.

The term "adapter" refers to an item configured so that it becomes possible to be combined with the restriction enzyme cleaving site of genomic DNA that is fragmented as shown in FIG. 2B. The configuration of such adapter comprises a restriction enzyme cleaving site (0201) that is composed of a single-chain portion and a core sequence site (0202) that is composed of a two-chain portion. The adapter for EcoRI and the adapter for MseI are used. The adapter for EcoRI comprises the EcoRI restriction enzyme cleaving site. And the adapter for MseI comprises the MseI restriction enzyme cleaving site. Base sequences and base numbers for the core sequence sites concerning two adapters mentioned above may conform to the descriptions in non-patent document 3. However, the base sequences and base numbers for the core sequence sites are not particularly limited, and arbitrary base sequences and base numbers for the core sequence sites are acceptable.

Any primers for selecting the *Aphanomyce cochlioides*-resistant plant variety can have base sequences other than those represented by any one of SEQ ID NOs: 1 through 5 on the 5'-end side and/or the 3'-end side as additional regions. In the case of an additional side on the 5'-end side, in relation to the base sequences of such additional region, the base sequences that are continuous with the 5' side of the n region in relation to the base sequences of the adapter are preferable as shown in FIGS. 2C and D. However, base sequences are not particularly limited to those mentioned above, and arbitrary base sequences are acceptable. Additionally, in the case of an additional region on the 3'-end side, the base sequences of such additional region are configured based on the base sequences on genomic DNA of genus *Beta* that are continuous with the 3' side of the G region. That is to say, such base sequences correspond to the complementary bases of N (0204) as shown in FIGS. 2C and 2D. Specifically speaking, such base sequences correspond to the base sequences of the polynucleotide represented by any one of claims 6 through 8 as stated below. And such base sequences on the 3' side are continuous with a region of sequences homologous with the base sequences of the G region, represented by any one of SEQ ID NOs: 1 through 5.

According to the method for selecting an *Aphanomyce cochlioides*-resistant plant variety of the present embodiment, the primer is a total of 17-25 bases in length, which allows for sufficient effects. Therefore, in case that the additional region mentioned above is applied to the primer for selecting the *Aphanomyce cochlioides*-resistant plant variety, it may be desirable for the additional region to be designed to be 1 base or more and within 8 bases so that all base numbers can be within 25 bases. A case where all base numbers of such primer correspond to less than 16 base sequences is not desirable because nonspecific hybridization tends to take place easily in regards to the base sequences of genomic DNA. Moreover, a case of 26 bases or more unnecessarily results in high primer costs and thus is not preferable.

It is desirable that any Tm values of the primer for selecting the *Aphanomyce cochlioides*-resistant plant variety be 50° C. or higher. This is because such temperature enhances the specificity of mold recognition.

The primer for selecting the *Aphanomyce cochlioides*-resistant plant variety may be labeled by fluorescent substances, labeled substances, RI (radioactive isotopes), or the like. This is because such labeling allows for easy detection of a polynucleotide amplified by the *Aphanomyce cochlioides*-resistant plant variety via the method for selecting an *Aphanomyce cochlioides*-resistant plant variety as stated below. The term "fluorescent substances" refers to the substances that enter excited states through absorption of excitation lights at specific wavelengths and discharge fluorescence when returning to the original ground states. For instance, examples include FAM, TET, HEX, Cy3, Cy5, Texas Red, FITC, and the like. Additionally, the term "labeled substances" refers to hapten and biotin of digoxigenin (DIG) and the like. The position of such primer labeled by the labeling substances mentioned above used for selecting the *Aphanomyce cochlioides*-resistant plant variety may be determined from time to time according to the nature of labeled substances to be used and the like. There are no particular limitations therefor. For instance, examples include 5'-end labeling based on a label of [$\gamma$-$^{33}$P] ATP using T4 polynucleotide kinase and the like. In regards to labeling of such primer, it may be sufficient to label at least one of the primer pair to be used. In order to increase sensitivity, the same label is acceptable for both primers. Alternatively, a different form of labeling is acceptable for both primers so that the same amplification product may be detected via a different means.

In addition, the method for selecting an *Aphanomyce cochlioides*-resistant plant variety of the present embodiment is based on the premise that the primer for selecting the *Aphanomyce cochlioides*-resistant plant variety exists in the form of a primer pair that comprises the base sequences represented by SEQ ID NOs: 1 and 2 (hereinafter referred to as the "first primer pair"), a primer pair that comprises the base sequences represented by SEQ ID NOs: 3 and 4 (hereinafter referred to as the "second primer pair"), and the primer pair that comprises the base sequences represented by SEQ ID NOs: 3 and 5 (hereinafter referred to as the "third primer pair").

The term "*Aphanomyce cochlioides*-resistant plant variety" refers to a plant variety with high resistance against infection with *Aphanomyce* as mentioned above. Such plant variety is of genus *Beta*, which is not affected by the *Aphanomyce cochlioides* or is affected thereby with difficulty, and which can be identified via the method for selecting an *Aphanomyce cochlioides*-resistant plant variety of the present invention. The term "plant variety" refers to a plant variety of *Beta vulgaris* L., such as Kabutomaru, Monohomare, Yukinohide, and the like, a plant variety hybridizable with a *Beta vulgaris* L. plant variety belonging to the genus *Beta*. When the *Aphanomyce cochlioides*-resistant plant variety of the present invention is explained genetically, such *Aphanomyce cochlioides*-resistant plant variety has at least one haplotype in which the dominant allele of the *Aphanomyce cochlioides*-resistant gene as the phenotype of resistance against *Aphanomyce cochlioides* exists. The term "of genus *Beta*" refers to *Chenopodiaceae Beta*, in general. However, the plant variety "of genus *Beta*" used in the present invention refers to plant species of genus *Beta* that can be hybridized with *Beta vulgaris* L. For instance, examples include *Beta vulgaris* L., table beet, spinach beet, swiss chard and fodder beet, and the like. From among plant species of genus *Beta*, in particular, *Beta vulgaris* L. satisfies the purposes of the present invention as a measure in regards to reduction of sugar yields resulting from *Aphanomyce cochlioides*.

The term "*Aphanomyce cochlioides*-resistant gene" refers to a gene existing on the genome of *Beta vulgaris* L., in which one of the alleles shows a high resistance dominant phenotype in regards to infection of *Aphanomyce*. Such gene has not been identified. However, as far as *Beta vulgaris* L. is concerned, it has been revealed that such gene exists on a third chromosome based on the results of QTL analysis shown in FIG. 5. Additionally, as shown in FIG. 7, the locus is also extrapolated. Therefore, in the present invention, as a matter of convenience, such gene corresponds to Acr1 (*Aphanomyce cochlioides* resistance 1). Also, the dominant allele of such gene that shows resistance to infection with *Aphanomyce* corresponds to $Acr1^r$. At the same time, the recessive allele of such gene that shows susceptibility to infection with *Aphanomyce* corresponds to $Acr1^s$. In addition, general *Beta vulgaris* L. is susceptible to *Aphanomyce cochlioides*. Thus, the genotype thereof corresponds to $Acr1^s$ homo state, that is to say, $Acr1^s/Acr1^s$ applies.

(Constituent Features Concerning Polynucleotides)

Any polynucleotides referred to herein comprise base sequences of some amplified fragments that have been specifically amplified based on the *Aphanomyce cochlioides*-resistant plant variety in the process of development of the method for selecting an *Aphanomyce cochlioides*-resistant plant variety of the present embodiment. Such base sequences are represented by any one of SEQ ID NOs: 6 through 8, or base sequences with homology of 90% or more with the base sequences represented by any one of SEQ ID NOs: 6 through 8. In regards to polynucleotides, whether they are single-stranded or double-stranded is not significant. Moreover, such base sequences exist on the genomic DNA of *Beta vulgaris* L. And such base sequences are strongly linked with Acr1 locus. Furthermore, such base sequences can be replaced with Acr1 on the genome of other varieties of genus *Beta* through hybridization.

Polynucleotides that comprise the base sequences represented by any one of SEQ ID NOs: 6 through 8 are specifically explained hereinafter.

Polynucleotides that comprise the base sequences represented by SEQ ID: 6 are composed of 135 bases. Such polynucleotides comprise certain amplified fragments that have been specifically amplified based on the *Aphanomyce cochlioides*-resistant plant variety in the process of development of the method for selecting an *Aphanomyce cochlioides*-resistant plant variety of the present embodiment using the first primer pair mentioned above. The cleaving terminal sequence of MseI (5'-TAA-3'; the same shall be applied hereinafter) and the cleaving terminal sequence of EcoRI (5'-AATTC-3'; the same shall be applied hereinafter) exist on the ends of such polynucleotides.

Polynucleotides that comprise the base sequences represented by SEQ ID: 7 are composed of 172 bass. Such polynucleotides comprise certain amplified fragments which have been specifically amplified based on the *Aphanomyce cochlioides*-resistant plant variety in the process of development of the method for selecting an *Aphanomyce cochlioides*-resistant plant variety of the present embodiment using the second primer pair mentioned above. The cleaving terminal sequences of MseI and EcoRI exist on the ends of such polynucleotides in the same manner as those of the polynucleotides represented by SEQ ID: 6. In addition, the base sequences represented by "n" correspond to undetermined base sequences.

Polynucleotides that comprise the base sequences represented by SEQ ID: 8 are composed of 307 base sequences. Such polynucleotides comprise certain amplified fragments that have been specifically amplified based on the *Aphanomyce cochlioides*-resistant plant variety in the process of development of the method for selecting an *Aphanomyce cochlioides*-resistant plant variety of the present embodiment using the third primer pair mentioned above. The cleaving terminal sequences of MseI and EcoRI exist on the ends of such polynucleotides in the same manner as those of the polynucleotides represented by SEQ ID: 6.

The term "base sequences with homology of 90% or more with the base sequences represented by any one of SEQ ID NOs: 6 through 8" refers to the base sequences that share identity of 90% or more with the base sequences represented by any one of SEQ ID NOs: 6 through 8 through deletion, substitution, addition, or the like of the base sequences represented by any one of SEQ ID NOs: 6 through 8 mentioned above. The term "deletion" refers to base sequences represented by any one of SEQ ID NOs: 7 through 9 in which more than one of the base sequences have been lost. Additionally, the term "substitution" refers to base sequences represented by any one of SEQ ID NOs: 6 through 8 in which more than one or two consecutive bases have been substituted with different bases. For instance, examples include point mutation, inversion, or overlapping, insertion, or translocation accompanying deletion. Furthermore, the term "addition" refers to base sequences represented by any one of SEQ ID NOs: 6 through 8 in which more than one of consecutive base sequences that do not constitute the entirety thereof have been newly added. For instance, examples include insertion, overlapping, or translocation not accompanying deletion.

Some or all of such polynucleotides and the base sequences thereof can be used as indicators, primers, or probes in order to detect the *Aphanomyce cochlioides*-resistant plant variety via the method for selecting an *Aphanomyce cochlioides*-resistant plant variety. For instance, an example related to an indicator used to detect the *Aphanomyce cochlioides*-resistant plant variety includes use of the AFLP method. In this method, base length is used. Details regarding this matter shall be provided in connection with the process of detection via the method for selecting an *Aphanomyce cochlioides*-resistant plant variety.

Additionally, for instance, examples of primers used to detect the *Aphanomyce cochlioides*-resistant plant variety include SNP located at an end restriction site of the corresponding polynucleotides in which the base sequences of SNP linked with $Acr1^r$ are substituted by LNA (Locked Nucleic Acid). Making use of the high boding affinity and thermostability of LNA's complementary nucleobases, the primer in question selectively amplifies the base sequence loci linked with $Acr1^r$ from the genomic DNA of genus *Beta* based on temperature difference hybridization conducted upon mold DNA. Based on the presence or absence of amplified products, a method for identifying the *Aphanomyce cochlioides*-resistant plant variety is given.

Furthermore, examples of probes used to detect the *Aphanomyce cochlioides*-resistant plant variety include a probe in which the base sequences of SNP linked with $Acr1^r$ are substituted by PNA (Peptide Nucleic Acid) associated with SNP located at end restriction sites of the corresponding polynucleotides. Making use of the thermostability of PNA's complementary nucleobases and high selectivity concerning the base sequences, a method is provided that involves specific hybridization of the probe in question including SNP linked with $Acr1^r$ based on temperature difference associated with genome fragments of genus *Beta*. Such method also is used to identify the *Aphanomyce cochlioides*-resistant plant variety. There also exists a method that selectively amplifies the base sequence loci linked with $Acr1^r$ from the genomic DNA of genus *Beta* via a PCR clamping method using the corresponding probe.

The term "seeds having resistance against the *Aphanomyce cochlioides* and/or progenies of the *Aphanomyce cochlioides*-resistant plant variety" refers to seeds and/or progenies produced through hybridization or cloning using the *Aphanomyce cochlioides*-resistant plant variety with more than one of polynucleotide(s) selected from among the polynucleotides that comprise the base sequences represented by any one of SEQ ID NOs: 6 through 8, or base sequences with homology of 90% or more with the base sequences represented by any one of SEQ ID NOs: 6 through 8. And such seeds and/or progenies have $Acr1^r$. The term "seeds and/or progenies created through cloning" refers to cloned seeds and/or cloned progenies with the same genetic information acquired through cultivation of some tissues of the *Aphanomyce cochlioides*-resistant plant variety mentioned above. For instance, publicly known dedifferentiation treatment is conducted for tissues acquired from the root potions of the *Aphanomyce cochlioides*-resistant plant variety, and callus induction is performed thereon. Thereafter, cloned seeds and/or cloned progenies acquired through cultivation of such callus apply.

(Constituent Features of the Method for Selecting an *Aphanomyce Cochlioides*-Resistant Plant Variety)

The method for selecting an *Aphanomyce cochlioides*-resistant plant variety is a method for amplifying nucleic acids in a selective manner based on the AFLP method that comprises a DNA extraction process, a DNA cleaving process, a process for amplifying nucleic acids, and a detection process. Details of the aforementioned processes are specifically explained hereinafter.

A DNA extraction process corresponds to a process for extracting of DNA from tissues of genus *Beta*. DNA extracted via the DNA extraction process is acceptable as long as it contains genomic DNA. Such DNA is acceptable even if it is mixed with mitochondrial DNA or chloroplast DNA, and, in fact, in the case of all DNA. This is because genomic DNA is necessary as a mold at the processes following the DNA extraction process. Any tissues of genus *Beta* are acceptable, such as leaf portions, stalk portions, root portions, or the like, as long as such tissues are of plants of genus *Beta*. This is because genomic DNA as a mold is contained in all such tissues. A leaf portion is preferable. This is due to the fact that, because genomic DNA in tissues are hardly susceptive to fragmentation by a DNA-degrading enzyme thereof, it is easy to extract the same, damages caused to plants upon extraction are minimal, and the like. Additionally, tissues of genus *Beta* that have been frozen immediately following extraction of plants may be used. This is because, based on the freezing treatment, genomic DNA in tissues are hardly susceptive to enzymatic degradation.

A DNA cleaving process a process for cleaving of extracted DNA using a restriction enzyme. The term "restriction enzyme" of the present embodiment refers to the combined form of EcoRI and EcoRI isoschizomer, or MseI and MseI isoschizomer, according to the AFLP method stated in non-patent document 3. The method for selecting an *Aphanomyce cochlioides*-resistant plant variety of the present embodiment utilizes a difference of patterns of restriction enzyme cleaving between the *Aphanomyce cochlioides*-resistant plant variety and the *Aphanomyce cochlioides*-susceptible plant variety as a result of cleaving the genomic DNA of genus *Beta* using the two different types of restriction enzymes mentioned above. That is to say, the method for selecting an *Aphanomyce cochlioides*-resistant plant variety of the present embodiment is a method for using SNP linked with Acr1 (single nucleotide type) in regards to genomic DNA of genus *Beta* located within the restriction sites of EcoRI and/or MseI, and such SNP differs from $Acr1^r$ and $Acr1^s$.

A process for amplifying nucleic acids corresponds to a process for amplifying nucleic acids using a prime pair mentioned above based on the genomic DNA fragments as the molds acquired through the DNA cleaving process mentioned above. The method for selecting an *Aphanomyce cochlioides*-resistant plant variety of the present embodiment is based on the AFLP method stated above. Thus, such process for amplifying nucleic acids is composed of several phases of processes. Details of such matters are explained in the portion hereof relating to the method of the present embodiment.

The term "genomic DNA fragments" refers to genomic DNA fragments with various lengths acquired after the DNA cleaving process mentioned above. The end portions of such genomic DNA fragments correspond to the end portions cut by the used restriction enzyme. That is to say, the 5'-end and the 3'-end correspond to the end cut by the EcoRI or EcoRI isoschizomer and/or the end cut by the MseI or MseI isoschizomer. The corresponding genomic DNA fragments function as molds used in the process for amplifying the nucleic acids in question.

The term "amplifying of nucleic acids" refers to amplifying of specific regions pinched between two primers due to enzyme reaction based on DNA or the like as a mold. A method for amplifying nucleic acids is called "a nucleic acid amplification method." Specific examples thereof include the PCR method, ICAN method, LAMP method, NASBA method, and the like. As a mold, primer, and adapter, the method for selecting an *Aphanomyce cochlioides*-resistant plant variety of the present embodiment uses genomic DNA fragments acquired through the DNA cleaving process mentioned above, the pairs of the primers for selecting the *Aphanomyce cochlioides*-resistant plant variety mentioned above, and the adapter for the AFLP method as stated below, respectively.

The term "detection process" refers to a process for detecting of polynucleotides that contain the base sequences of polynucleotides listed in any one of claims 6 through 8 (hereinafter referred to as "amplified polynucleotides") from among the nucleic acids amplified through the process for amplifying nucleic acids mentioned above. Specifically, the detection process detects the polynucleotides as follows. That is to say, in a case in which the first primer pair is used, a polynucleotide that contains the base sequences represented by SEQ ID: 6 and base sequences with homology of 90% or more with base sequences represented by SEQ ID: 6 are detected. In a case in which the second primer pair is used, a polynucleotide that contains the base sequences represented by SEQ ID: 7 and base sequences with homology of 90% or more with the base sequences represented by SEQ ID: 7 are detected. And in a case in which the third primer pair is used, a polynucleotide that contains the base sequences represented by SEQ ID: 8 and base sequences with homology of 90% or more with base sequences represented by SEQ ID: 8 are detected.

The term "amplified polynucleotides" refers to the polynucleotides that comprise (a) a base sequence of any one of the polynucleotides listed in the constituent features of the polynucleotides; that is to say, the base sequences of the polynucleotides according to any one of claims 6 through 8; and furthermore, (b) a base sequence to which the adapter sequence for the primer for selecting the *Aphanomyce cochlioides*-resistant plant variety used through the process for amplifying nucleic acids mentioned above is added to both the 5'- and 3'-end portions. Therefore, the base lengths of such amplified polynucleotides are long given the extent of addition of adapter sequences. Such amplified polynucleotides are specifically amplified due to the genomic DNA which is derived strain that has Acr1$^r$ in a homo or hetero state. And such amplified polynucleotides are normally not amplified by the genomic DNA which is derived from a Acr1$^r$ homo individual. That is to say, whether or not such amplified polynucleotides can be detected allows judgment as to whether a strain as a target of detection corresponds to the *Aphanomyce cochlioides*-resistant plant variety.

However, the method for selecting an *Aphanomyce cochlioides*-resistant plant variety of the present embodiment corresponds to a method for making use of SNP that is strongly linked with Acr1 and differs between Acr1$^r$ and Acr1$^s$, and of indirectly determining the presence or absence of Acr1$^r$. Therefore, in case that crossover occurs to Acr1 and such SNP, it is also possible to detect an Acr1$^r$ home individual; that is to say, the amplified polynucleotides of the genomic DNA derived from the *Aphanomyce cochlioides*-susceptible plant variety. The frequency with which so-called false detection takes place matches the RV (Recombination Value) with Acr1 and SNP mentioned above. That is to say, the frequency with which false detection takes place is about 2.2% for Acr1 and SNP in the case of using the first primer pair, about 4.3% for Acr1 and SNP in the case of using the second primer pair, and about 4.3% between Acr1 and SNP in the case of using the third primer pair. Such frequency is remarkably low compared with the frequency of false detection with the conventional method for selecting an *Aphanomyce cochlioides*-resistant plant variety depending on the phenotype (about 50%). Additionally, in case that resistance of *Aphanomyce cochlioides* is actually detected, rather than performing an examination using only one prime pair for a single individual, detection is conducted using of two or three primer pairs. Therefore, in the case of using of three primer pairs, the frequency of false detection based on the method for selecting an *Aphanomyce cochlioides*-resistant plant variety of the present embodiment is about 0.004% (0.022×0.043× 0.043). This is an ignorable value. Therefore, the frequency of false detection occurring due to crossover of Acr1 and SNP lined therewith does not reduce the effects of the method for selecting an *Aphanomyce cochlioides*-resistant plant variety of the present embodiment at all.

(Constituent Features of the *Aphanomyce Cochlioides*-Resistant Plant Variety and the Like of the Present Embodiment Acquired Through the Method for Selecting an *Aphanomyce Cochlioides*-Resistant Plant Variety of the Present Embodiment)

The term "the *Aphanomyce cochlioides*-resistant plant variety and the like" refers to an *Aphanomyce cochlioides*-resistant plant variety of genus *Beta*, progenies of the *Aphanomyce cochlioides*-resistant plant variety of genus *Beta*, and seeds having resistance against the *Aphanomyce cochlioides* of genus *Beta*.

The meaning of the term "method for producing of seeds having resistance against the *Aphanomyce cochlioides* of genus *Beta* and/or progenies of the *Aphanomyce cochlioides*-resistant plant variety of genus *Beta* through hybridization or cloning" is not particularly restricted as long as a corresponding hybridization or cloning method can produce seeds and/or progenies.

First Embodiment

Method

Figure 3:
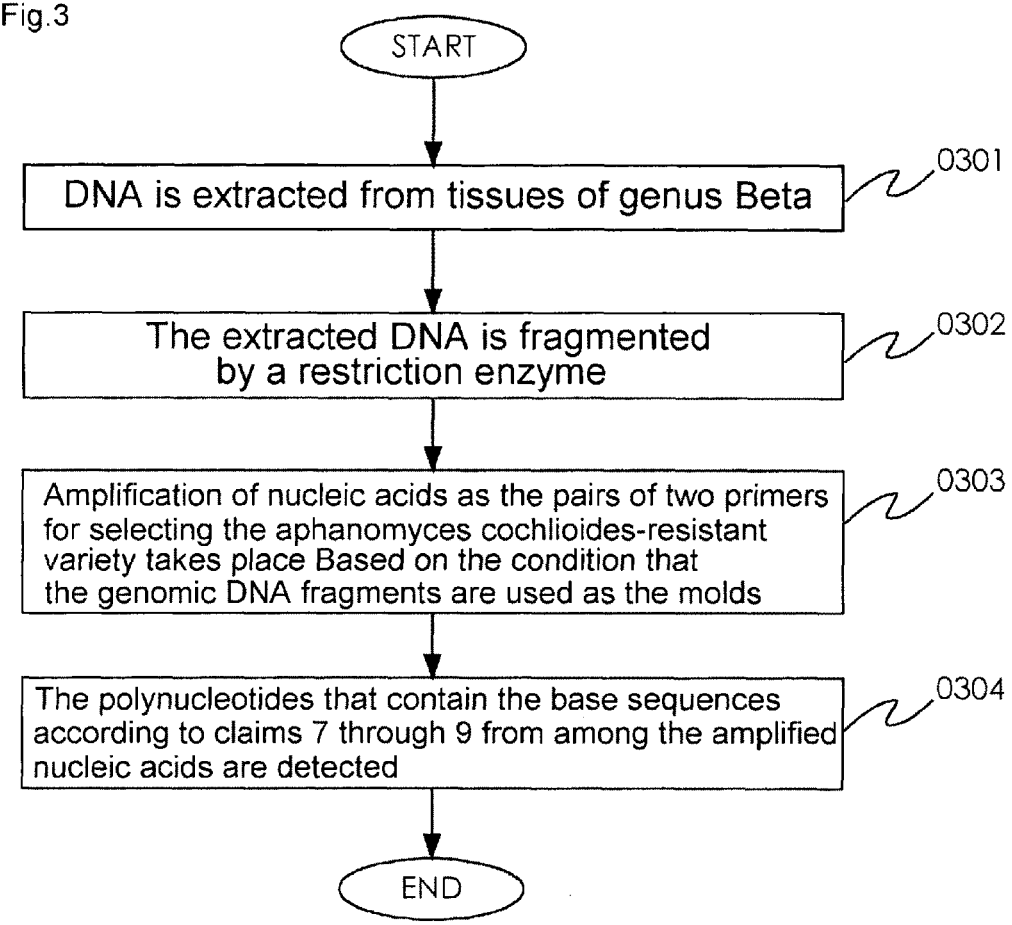
FIG. 3 is an explanatory figure concerning the flow of phases of the method for selecting an *Aphanomyces cochlioides*-resistant plant variety of the first embodiment.

FIG. 3 shows one example of the process flow of the method for selecting an *Aphanomyce cochlioides*-resistant plant variety of the first embodiment. First of all, DNA is extracted from tissues of genus *Beta* (S0301: DNA extraction process). Subsequently, the extracted DNA is fragmented by a restriction enzyme (S0302: DNA fragmentation process). Next, amplification of nucleic acids as the pairs of two primers for selecting the *Aphanomyce cochlioides*-resistant plant variety mentioned above takes place, based on the condition that the genomic DNA fragments acquired through the DNA extraction process mentioned above are used as the molds (S303: process for amplifying nucleic acids). Finally, the polynucleotides that contain the base sequences according to claims 1 through 8 from among the nucleic acids amplified through the process for amplifying nucleic acids mentioned above are detected (S0304: detection process). After experiencing the above processes, the *Aphanomyce cochlioides*-resistant plant variety suitable for a given purpose can be selected.

The method for selecting an *Aphanomyce cochlioides*-resistant plant variety of the first embodiment is based on the AFLP method. That is to say, such method corresponds to a method for detecting the presence or absence of SNP linked with the *Aphanomyce cochlioides*-resistant gene. Such SNP differs between Acr1$^r$ and Acr1$^s$. Basic techniques and methods related to the method for selecting an *Aphanomyce cochlioides*-resistant plant variety of the first embodiment may conform to the publicly known AFLP method. The methods concerning each process are specifically explained hereinafter.

(1) DNA Extraction Process (S0301)

A method for extracting DNA is not particularly restricted as long as it allows the genomic DNA to be extracted from tissues of genus *Beta*. Specific examples include the CTAB (cetyltrimethylammonium bromide) method. One example of this specific method is given in detail in connection with first embodiment. In addition to such method, as far as DNA extraction is concerned, commercially available DNA preparation kits, such as ISOPLANT (NIPPON GENE), may be used.

(2) DNA Cleaving Process (S0302)

Cutting of DNA is conducted based on two types of restriction enzymes, that is to say, EcoRI and MseI, or a combination of an isoschizomer therewith. In relation to such restriction enzymes, it is sufficient to use commercially available restriction enzymes. Additionally, buffer composition, salt concentration, pH, and the like, in relation to the restriction enzymes, may be determined in conformance with the reaction conditions used in general. In relation to the quantity of restriction enzymes used for reaction, based on the DNA quantity to be used for reaction, a relevant quantity of enzymes that allows for sufficient cleaving of the DNA quantity is determined accordingly. For instance, in the case of a quantity of DNA of 1 µg, about 2 to 3 units from each of EcoRI and MseI may be used. The precedence order for cleaving the restriction enzymes is not particularly significant. For instance, cleaving can be conducted simultaneously with EcoRI and MseI. Alternatively, after cleaving is conducted with one of the restriction enzymes, another restriction enzyme may be used for cleaving. In regards to reaction temperature and reaction time, conditions that allow the genomic DNA to be sufficiently fragmented are appropriately selected according to the DNA quantity to be used for reaction. For example, in the case of using of 2 units of restriction enzymes for 1 µg of DNA, 37° C. as a reaction temperature and 1 to 2 hours of reaction time may be selected. Following the cleaving reaction, in order to prevent recombination of cleaved end portions, a condition is preferable such that the reaction solution is heated once to about 70° C. to 80° C., following which such solution is quenched to 4° C. or lower.

(3) Process for Amplifying Nucleic Acids (S303)

Figure 4:
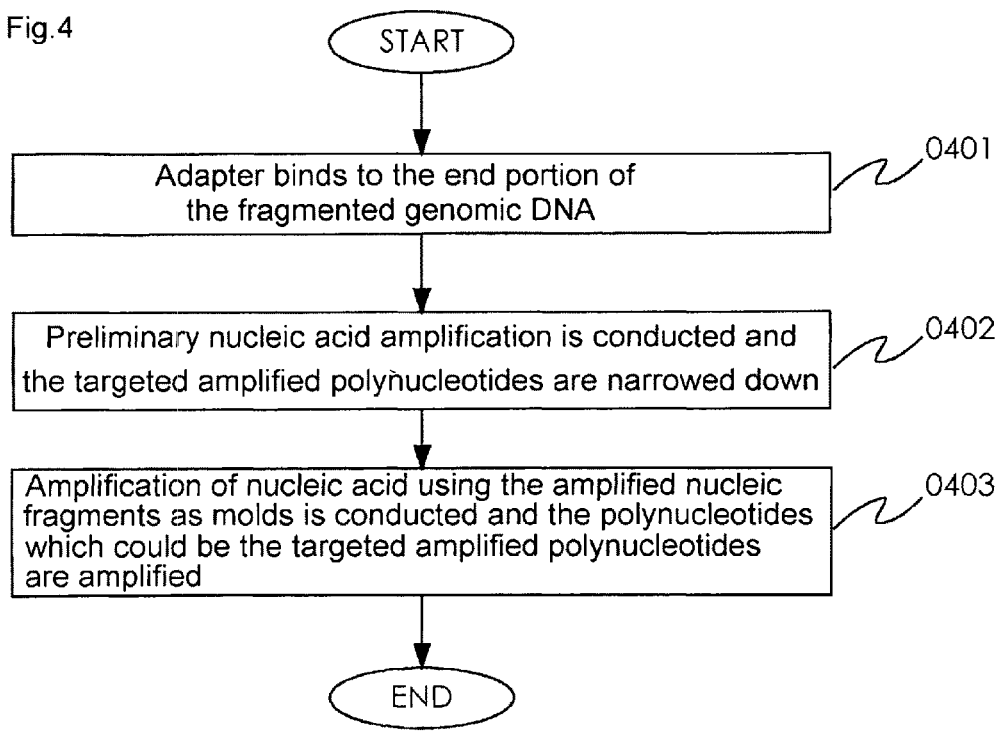
FIG. 4 is an explanatory figure concerning a flow of phases that comprise a process for amplifying nucleic acids via the method for selecting an *Aphanomyces cochlioides*-resistant plant variety of the first embodiment.

The method for selecting an *Aphanomyce cochlioides*-resistant plant variety of the first embodiment is based on the AFLP method. Thus, the process for amplifying nucleic acids is composed of processes at a plurality of phases. Normally, three phases, as shown in FIG. 4, are desirable. However, the number of phases is not particularly restricted as long as the polynucleotides as a target can be amplified in an efficient manner. For instance, the process for amplifying nucleic acids may be composed of two phases of an adapter binding process for the first phase and a selection process for the third phase. The present embodiment is explained hereinafter with the assumption of three phases.

(First Phase: Adapter Binding Process)

The first phase corresponds to an adapter binding process (S0401). This process is characterized by the fact that an adapter is bonded with the end portion of the genomic DNA fragmented through restriction enzymes. In regards to binding, a DNA binding reaction method using T4 DNA ligase is common and convenient. Buffer composition, salt concentration, pH, and the like, in relation to T4 DNA ligase, may be selected in conformance with the reaction conditions used in general. In regards to an adapter, two of an EcoRI adapter and MseI adapter are used. Additionally, it is preferable to apply an equal amount of the adapter quantities to be added. It is acceptable for the binding reaction temperature to fall within a scope of 8° C. to 30° C. However, a reaction temperature within a scope of 15° C. through 20° C. is more desirable. The lower the binding reaction temperature, the longer the reaction time. For instance, in the case of 20° C., about 2 hours of reaction time is acceptable. When 10° C. applies, a reaction of about 12 hours is necessary. Adapter biding is not limited by the method mentioned above. Any method is acceptable as long as the adapter binding to the end portions of the fragmented genomic DNA is possible. Moreover, in recent years, DNA binding reaction kits using various enzymes and the like have become commercially available. And it is also acceptable to use the same. In such case, reaction conditions and the like may be selected in conformance with the protocol attached thereto.

(Second Phase: Preliminary Amplification Process)

The second phase corresponds to a preliminary amplification process (S0402). The purpose of such process is to conduct preliminary nucleic acid amplification using a pair of primers for preliminary amplification of the *Aphanomyce cochlioides*-resistant plant variety and to narrow down the targeted amplified polynucleotides.

A primer for preliminary amplification of the *Aphanomyce cochlioides*-resistant plant variety comprises complementary bases and specific bases allocated on the 3'-end side for the two types of the adapters mentioned above, respectively. Complementary base sequences herein comprise the base sequences of some or all of the EcoRI or MseI restriction sites, some or all of the core sequences adjacent thereto, and complementary base sequences. The number of bases of the complementary base sequences of the adapters is not particularly restricted, as long as such number of bases is greater than 13. Additionally, specific bases comprise one or more bases. Normally, one base may be sufficient. The ATGC that is applied in regards to such specific bases is determined based on the primer pair used for selecting the *Aphanomyce cochlioides*-resistant plant variety to be used for the subsequent third phase. That is to say, such specific bases correspond to the bases adjacent to the 3'-end side (side of direction of extension) of the base sequences of some or all of the restriction sites of EcoRI or MseI contained in the primer for selecting the *Aphanomyce cochlioides*-resistant plant variety to be used. For instance, in case that primer pairs for selecting the *Aphanomyce cochlioides*-resistant plant variety to be used for the third phase contain SEQ ID NOs: 1 and 2, the primer for selecting the *Aphanomyce cochlioides*-resistant plant variety containing SEQ ID: 1 includes AATTC, which constitutes a part of the restriction site of EcoRI. Therefore, the base that is adjacent to the 3' end C of such restriction site from the base sequence represented by SEQ ID: 1 is G. In the same manner, the primer for selecting the *Aphanomyce cochlioides*-resistant plant variety containing SEQ ID: 2 includes TAA, which constitutes a part of the restriction site of MseI. Therefore, the base that is adjacent to the 3' end A of such restriction site from the base sequence represented by SEQ ID: 2 is C.

Any nucleic acid amplification method may be used for the process for amplifying nucleic acids as long as it allows amplification of the targeted polynucleotides. For instance, examples include the PCR method, ICAN method, LAMP method, and the like. The various PCR methods are the most established and convenient methods. In regards to reaction conditions of the nucleic acid amplification method, such as reaction temperature, cycle number, and the like, it is acceptable for ideal conditions to be determined appropriately in accordance with publicly known techniques based on the different methods mentioned above. In this specification, reaction conditions in the case of using the PCR method are used as an example in connection with the first example as described below. Of course, other conditions are not restricted thereby.

(Third Phase: Selection Process)

The third phase involves a selection process (S0403). The characteristics of this process involve the further carrying out of nucleic acid amplification based on the condition that the nucleic acid fragments amplified through the preliminary amplification process mentioned above using primer pairs for selecting the *Aphanomyce cochlioides*-resistant plant variety as a mold, and amplification with the amplified polynucleotides as a target.

It is convenient to implement the nucleic acid amplification method and the reaction conditions to be used for the selection process in accordance with the nucleic acid amplification method of the second phase mentioned above. Additionally, it is not necessary for the nucleic acid amplification method to be used herein to be the same method as that of the second phase mentioned above. For example, a PCR method may be used for the preliminary amplification process of the first phase, and a method may be used that is based on a combination of different nucleic acid amplification methods, such as using an ICAN method for the selection process of the third phase and the like. Specific procedures and reaction conditions for each method may be selected in accordance with publicly known techniques. In this specification, reaction conditions in the case of using the PCR method are used as an example in connection with the first example as described below. Of course, other conditions are not restricted thereby.

As mentioned above, the solution of the final amplified product acquired through such process for amplifying nucleic acids is used for the subsequent detection process.

(4) Detection Process (S0304)

It is convenient to use a gel electrophoresis method for detecting the amplified polynucleotides. In the case of using a primer pair for selecting the *Aphanomyce cochlioides*-resistant plant variety of the present embodiment, if any pairs are used, the polynucleotides with the same approximate base length as that of the amplified polynucleotides in relation to the *Aphanomyce cochlioides*-susceptible plant variety cannot be detected (excluding a case of occurrence of crossover of Acr1 and SNP linked therewith, and the same shall be applied hereinafter). In accordance with the gel electrophoresis method, the existence of *Aphanomyce cochlioides*-resistant plant variety can be easily judged depending upon presence or absence of the base lengths of the amplified polynucleotides. Additionally, another reason why the gel electrophoresis method is desirable is that those who work in the molecular biological field can easily implement the same without needing to learn or acquire special techniques.

As stated above, in relation to the base length of the amplified polynucleotides, adapter sequences of the primers used for the process for amplifying nucleic acids are added to both ends of the base sequences of the polynucleotides according to any one of claims 6 through 8. The added base length belongs within the scope of 20 through 36 bases, which are based on the combination of the adapter sequences of both ends. As a specific example, in the case of detecting of the amplified polynucleotides containing the base sequences of the polynucleotides represented by SEQ ID: 7 using the first primer pair, the base length of such polynucleotides to be detected belongs within the scope of 155 through 171 bases. However, in case that variation, such as deletion, substitution, addition, or the like, takes place within the base sequences of the genomic DNA as a mold, the base length fluctuates accordingly.

In the case of detecting the amplified polynucleotides using of the gel electrophoresis method, if the polynucleotides to be detected have fewer than 500 bases, it is desirable to use the PAGE method. In such case, the concentration of acrylamide in the running gel (ratio by weight of acrylamide/bis-acrylamide=30/0.8) is established appropriately within a scope of 10% or more and 15% or less according to the base length of the amplified polynucleotides to be detected. Use of a stacking gel is optional. When it is used, a concentration of 5% acrylamide (ratio by weight of acrylamide/bis-acrylamide=30/0.8) can be applied.

The quantity of the sample applied to the gel may be determined appropriately based on the quantity of amplified polynucleotides to be detected. This quantity is not particularly limited. 5 µl/well of the solution of the amplified product acquired through the selection process concerning process for amplifying nucleic acids may be sufficient in general. As needed, about 1 µl of loading buffer may be added to 5 µl of the solution of the amplified product as needed.

Electrophoresis is conducted for about 3 hours at 280 V in the loading buffer (1×TBE and the like). At this time, electrophoresis is also performed regarding a size marker at the same time. It is convenient to use commercially available size marker, such as 100-bp DNA Ladder Marker (Takara) and the like.

In addition, in the course of conducting the detection process, in order to determine the nature of the amplified polynucleotides, it is preferable to use genomic DNA in which the genetic form has been revealed as a negative control ($Acr1^s$ homo) and positive control (or $Acr1^r$ homo or $Acr1^r$ hetero).

In regards to a confirmation method for the polynucleotides following the gel electrophoresis method, there exist: a method for using of at least one of the pairs of the primers for selecting the *Aphanomyce cochlioides*-resistant plant variety as stated above that is directly labeled by fluorescent substances or RI in advance for the process for amplifying nucleic acids as mentioned above; a method for conducting indirect fluorescent substance labeling using avidin protein or antibody that has been indirectly labeled, such as biotin, DIG, and the like; and a method for dyeing the polynucleotides existing in the gel following electrophoresis with a florescent substance in which intercalation is possible, such as Ethidium bromide, VistraGreen (Amersham), SYBER Green (registered trademark: Roche), and the like. In the case of labeling or dyeing with a fluorescent substance, the gel is exposed to light of the excitation wavelength of the used fluorescent substance following electrophoresis. And the chemiluminescence caused thereby can allow viewing of the polynucleotides in the gel. It is acceptable to visually confirm the chemicaluminescence if the luminescence intensity of the chemicaluminescence is viewable. Additionally, in case that the luminescence intensity is feeble, visual confirmation may be conducted with a biochemical chemicaluminescence photographic apparatus (Light Capture). In the case of labeling through RI, after appropriate treatment of the gel following electrophoresis, it is possible to conduct visual confirmation concerning the polynucleotides in the gel through exposure of the gel to X-ray film, an imaging plate (FUJIFILM), or the like. The basic operations for all such items are public techniques, and the details thereof may be performed in accordance with the relevant protocols.

Usually, in accordance with the primers pairs for selecting the *Aphanomyce cochlioides*-resistant plant variety as stated above, the approximate base length of the amplified polynucleotides in the *Aphanomyce cochlioides*-susceptible plant variety cannot be detected. Thus, judgment is possible via the gel electrophoresis method. However, in case that variation, such as deletion, addition, or the like, of a portion exceeding 40 bases within a region of the genomic DNA detected through such the primer pairs for selecting the *Aphanomyce cochlioides*-resistant plant variety takes place, there is a possibility that the base length of the amplified polynucleotides may be approximately the same as those of other nonspecific polynucleotides that are amplified in the *Aphanomyce cochlioides*-susceptible plant variety. In such case, it is possible to selectively detect the amplified polynucleotides using a hybridization method as a probe of some or all of the polynucleotides in any one of claims 6 through 8.

In regards to the hybridization method used herein, it is convenient to use the Southern hybridization method or publicly known methods based on the aforementioned method. A basic concept of the general Southern hybridization involves transcription of the polynucleotides fractionated in the gel following electrophoresis, hybridization of the labeled probe concerning the polynucleotides as the targets on the corresponding membrane, and detection of the same. This method requires techniques that are very common in the molecular biological field, and it is sufficient to conduct such method in accordance therewith in the present embodiment. Thus, detailed explanations are omitted.

In regards to the base sequences of the polynucleotides as probes, some or all of the base sequences of the polynucleotides represented by claim 6 are used in the case of using the first primer pair. Some or all of the base sequences of the polynucleotides represented by claim 7 are used in the case of using the second primer pair. And some or all of the base sequences of the polynucleotides represented by claim 8 are used in the case of using the third primer pair. Labeling of the probes may be conducted in accordance with a method of direct labeling of such primers with florescent substances and labeled substances, or RI. Additionally, detection of hybridized probes is appropriately conducted according to relevant determination based on the labeling of such probes. This may be conducted in accordance with the method of detecting of the primer for selecting the *Aphanomyce cochlioides*-resistant plant variety which has been labeled as mentioned above.

When using a single prime pair in the method for selecting an *Aphanomyce cochlioides*-resistant plant variety of the present embodiment, in case that it has been possible to detect amplified polynucleotides, it would be possible to judge, with 95% accuracy, that the corresponding individuals are of the *Aphanomyce cochlioides*-resistant plant variety. Additionally, upon independently using three primer pairs, in case that it has been possible to detect polynucleotides with prescribed base lengths for all such primer pairs, it would be possible to judge the individuals thereof to be the *Aphanomyce cochlioides*-resistant plant variety with almost 100% accuracy.

First Embodiment

Effect

In accordance with the primer for selecting the *Aphanomyce cochlioides*-resistant plant variety and the method for selecting an *Aphanomyce cochlioides*-resistant plant variety using such primer of the present embodiment, even during the seedling plant period prior to symptom development, it is possible indirectly select a plant variety that shows dominant resistance against *Aphanomyce cochlioides* in a highly accurate manner without depending on phenotype solely by collecting parts of the plants.

Moreover, the method for selecting an *Aphanomyce cochlioides*-resistant plant variety of the present invention can be used for selecting the *Aphanomyce cochlioides*-resistant progenies acquired through the selected *Aphanomyce cochlioides*-resistant plant variety. Thereby, it is possible to efficiently improve the breeding of *Beta vulgaris* L. with *Aphanomyce cochlioides* resistance without enormous effort, time, or costs. Due to this, it is possible that the sugar yields will not be majorly reduced by the illness. A stable supply of *Beta vulgaris* L. to the sugar manufacturing market becomes possible. That is to say, according to the present embodiment, ample effects in the sugar manufacturing industry will be remarkably high.

Second Embodiment

Outline

The second embodiment is related to a methodology for identifying Acr1 of the *Aphanomyce cochlioides*-resistant gene. The method for selecting an *Aphanomyce cochlioides*-resistant plant variety of the first embodiment mentioned above is the method for detecting of the amplified polynucleotides based on the SNP linked with Acr1 via the AFLP method. In addition, in the process of development of such method for selecting an *Aphanomyce cochlioides*-resistant plant variety, based on the segregation ratio of the phenotype of *Beta vulgaris* L. and the amplified polynucleotides of such *Beta vulgaris* L., it is possible to compute a Recombination Value between locus of Acr1 in regards to the genomic DNA of genus *Beta*, and the base sequence loci having the base sequences according to any one of claims 6 through 8. Furthermore, based on such Recombination Value and Kosambi's mapping function, the genetic distance of the same can be computed. The present embodiment relates to a method for identifying the Acr1 gene on the genome based on base sequence loci having base sequences of the polynucleotides according to any one of claims 6 through 8 and the aforementioned genetic distance.

Second Embodiment

Configuration

The second embodiment comprises and an methodology for identification of an *Aphanomyce cochlioides*-resistant gene, which identifies Acr1 using of the base sequence loci having the base sequences according to any one of claims 6 through 8, and the genetic distance between the base sequence loci having the base sequences according to any one of claims 6 through 8 and Acr1 loci, on the genomic DNA of genus *Beta*. The configuration of the present embodiment is specifically explained hereinafter.

The base sequence loci of the present embodiment correspond to a region with the base sequence represented by SEQ ID: 6 and any base sequence with homology of 90% or more with such sequence (hereinafter referred to as the "base sequences according to claim 6"); the base sequence represented by SEQ ID: 7 and any base sequence with homology of 90% or more with such sequence (hereinafter referred to as the "base sequences according to claim 7"); and the base sequence represented by SEQ ID: 8 and any base sequence with homology of 90% or more with such sequence (hereinafter referred to as the "base sequences according to claim 8").

Additionally, as per Table 1, the genetic distance between the base sequence loci and Acr1 loci is about 2.2 cM in the case of a locus having the base sequences according to claim 6. The genetic distance between the base sequence loci and Acr1 loci is about 4.3 cM in the case of a locus having the base sequences according to claim 7. The genetic distance between the base sequence loci and Acr1 loci is about 4.3 cM in the case of a locus having the base sequences according to claim 8. Here, Table 1 shows the serial analysis results concerning Acr1 loci and the base sequence loci mentioned above. Cl. 6, Cl. 7, and Cl. 8 in Table 1 correspond to the base sequence loci with the base sequences according to claims 6, 7, and 8, respectively. And A and B show the locus or base sequence loci. Detection of the base sequence loci were conducted depending on the presence or absence of the amplified polynucleotides via the method of the present embodiment. And detection of the Acr1 loci was conducted depending on the phenotype. The "+" symbol in Table 1 indicates a case in which the amplified polynucleotides were detected or a case in which the resistance phenotype against the *Aphanomyce cochlioides* was confirmed. The "−" symbol therein indicates a case in which the amplified polynucleotides were not detected or a case in which the sensitivity phenotype against the *Aphanomyce cochlioides* was confirmed. For instance, explanations are given with reference to 1. The value of "++" for "A:B" corresponds to 73. Thus, the number of strains was 73 based on the fact that the amplified polynucleotides (A) having the base sequences according to claim 6 were detected (+), and the resistance phenotype in regards to the *Aphanomyce cochlioides* (B) was confirmed (+). Furthermore, the term "RV" refers to a recombination value, the term "cM" refers to centimorgans, and the term "S.E." refers to a standard error. Based on the results of this Table, a genetic linkage map for Acr1 and the base sequence loci can be represented as per FIG. 7.

TABLE 1

| | | A:B (Number of strains) | | | | | | S.E. | | S.E. |
|---|---|---|---|---|---|---|---|---|---|---|
| A | B | ++ | +− | −+ | −− | Total | RV (%) | (%) | cM | (%) |
| 1 Cl. 6 | Acr1 | 73 | 2 | 0 | 21 | 96 | 2.2 | 1.5 | 2.2 | 1.5 |
| 2 Acr1 | Cl. 7 | 71 | 2 | 2 | 21 | 96 | 4.3 | 2.1 | 4.3 | 2.1 |
| 3 Acr1 | Cl. 8 | 71 | 2 | 2 | 21 | 96 | 4.3 | 2.1 | 4.3 | 2.1 |

Second Embodiment

Method

Acr1 can be identified using of the base sequence loci having the base sequences according to claim 6, the base sequences according to claim 7, and the base sequence loci having the base sequences according to claim 8 mentioned above, and the genetic distance between such base sequence loci having such base sequences and Acr1 loci, on the genomic DNA of genus *Beta*. That is to say, use may be made of the fact that the genetic distance normally represented by 1 cM is equivalent to about 1 Mb (megabase=$1 \times 10^6$ bases) as a physical distance. For instance, on the genomic DNA of genus *Beta*, the genetic distance between such base sequence loci having the base sequences according to claim 6 and Acr1 loci is about 2.2 Mb. Thus, Acr1 is located at a distance of about 2.2 Mb from such base sequence loci, on either the left or the right side thereof.

One example of a method for identifying Acr1 using the genetic distance mentioned above is explained hereinafter. First, regions homologous with the base sequences according to claim 6 mentioned above are searched for within the database of all genome base sequences of all varieties of genus *Beta*. In case that plant species correspond to *Beta vulgaris* L., only third chromosomes may be searched for. Subsequently, homologous regions acquired through the search mentioned above are the base sequence loci. Regarding such loci, a plurality of genes existing on the periphery of location at a physical distance of about 2.2 Mb from such base sequence loci, on either the left or the right side thereof, are selected as candidate genes. Determination of all base sequences concerning the candidate genes of the *Aphanomyce cochlioides*-resistant plant variety and the *Aphanomyce cochlioides*-susceptible plant variety is conducted. In case that there are more than 50 candidate genes, known genes or genes with predicted functions are selected. Furthermore, from among such selected genes, genes in which the link associated with the *Aphanomyce cochlioides* may be examined preferentially. In relation to the genes in which difference between the *Aphanomyce cochlioides*-resistant plant variety and the *Aphanomyce cochlioides*-susceptible plant variety can be discovered, in particular, in regards to the *Aphanomyce cochlioides*-susceptible plant variety, if there are genes in which the base sequences are differentiated depending on papuro type, such genes are selected as major potential candidates. Thereafter, in relation to the major potential candidates, the base sequences that cannot be discovered in the *Aphanomyce cochlioides*-resistant plant variety are linked to vectors as Acr1$^r$ allele candidates. Publicly known dedifferentiation treatment is given to the tissues acquired through the tissues of the *Aphanomyce cochlioides*-susceptible plant variety, and callus induction is conducted. Thereafter, the vectors linked with such genes are applied to the callus mentioned above through publicly known techniques. In case that the plants acquired through cultivation of callus show the phenotype of the *Aphanomyce cochlioides*-resistant plant variety, the Acr1$^r$ allele candidates are Acr1$^r$ genes as the targets and Acr1$^r$ allele genes with the resistance against *Aphanomyce cochlioides*.

A method in which a plurality of the base sequence loci, and the genetic distance between such plurality of base sequences loci and the Acr1 genetic loci are combined is preferable in regards to the methodology for identification of an *Aphanomyce cochlioides*-resistant gene. This is because, based on two or three points of base sequence loci, a single point of Acr1 genetic locus can be specified. That is to say, as per the linkage map as shown in FIG. 6, on the genomic DNA of genus *Beta*, the base sequence loci having the base sequences according to claim 6 and the Acr1 gene loci, and the base sequence loci having the base sequences according to claim 7 and the Acr1 gene loci mentioned are located 2.2 cM and 4.3 cM apart, respectively. Thus, the Acr1 genetic locus can be specified. Moreover, the distance between the base sequence loci having the base sequences according to claim 6 and the base sequence loci having the base sequences according to claim 7 is 6.5 cM. Comparing with such genetic distance and actual physical distance concerning the genome base sequences, the corrected physical distance between the base sequence loci and Acr1 genetic loci can be also computed. In addition, a methodology for identifying the genes may be implemented in the same manner as described above.

Second Embodiment

Effect

The methodology for identification of an *Aphanomyce cochlioides*-resistant gene of the present embodiment allows restriction of the regions that encode the *Aphanomyce cochlioides*-resistant gene on the genome, and identification of such genes. Additionally, making a comparison of the base sequences between the *Aphanomyce cochlioides*-resistant plant variety and the *Aphanomyce cochlioides*-susceptible plant variety, Acr1$^r$—that is to say, the *Aphanomyce cochlioides*-resistant allele of the *Aphanomyce cochlioides*-resistant gene—can be identified. In case that such gene can be identified, in regards to selection of the *Aphanomyce cochlioides*-resistant plant variety, it is possible to directly detect the same. Moreover, a gene recombinant in which the *Aphanomyce cochlioides*-resistant genetic allele is applied to the *Aphanomyce cochlioides*-susceptible plant variety is created. Due to this, it is possible to easily obtain an *Aphanomyce cochlioides*-susceptible plant variety.

First Example

The first embodiment is specifically explained hereinafter. The present embodiment simply exemplifies the present invention, and the present invention is not limited by such embodiment.

<Method for Selecting an *Aphanomyce Cochlioides*-Resistant Plant Variety>

Herein, in regards to 4 strains (a1-a4) of the plant variety that is revealed to have resistance against *Aphanomyce cochlioides* and 4 strains (b1-b4) of the plant variety that is revealed to have sensitivity in regards to *Aphanomyce cochlioides* based on phenotype, specific examples in which the method for selecting an *Aphanomyce cochlioides*-resistant plant variety of the first embodiment using plant issues (green leaves) acquired through each strain was implemented are described.

((Method))

(A) DNA Extraction Process

Herein, a method that involves use of the CTAB method is explained with reference to relevant examples.

(Reagent Composition)

2×CTAB: CTAB (ICN Biomedicals. Inc., and the same shall be applied hereinafter) 10 g, 1M Tris-HCl (pH8.0) 50 ml, 0.5M EDTA (pH8.0) 20 ml, polyvinylpyrrolidone (WAKO) 5 g, and NaCl of 40.9 g were mixed. Thereafter, sterile water was added to the mixed resultant such that it reached 500 ml.

10% CTAB: 50 g of CTAB and 20.45 g of NaCl were mixed. Thereafter, sterile water was added to the mixed resultant such that it reached 500 ml.

CTAB precipitation buffer solution: CTAB: CTAB 5 g, 1M Tris-HCl (pH8.0) 25 ml and 0.5M EDTA (pH8.0) 10 ml were mixed. Thereafter, sterile water was added to the mixed resultant such that it reached 500 ml.

High Salt TE Buffer: Nacl 58.4 g, 1M Tris-HCl (pH8.0) 10 ml and 0.5M EDTA (pH8.0) 2 ml were mixed. Thereafter, sterile water was added to the mixed resultant such that it reached 1,000 ml.

TE-RNase: 10 mg RNase A (WAKO) and TE 1 ml (CTAB Method)

(1) 0.3 to 0.5 g of leaves (green leaves) was prepared. After the leaves to which liquid nitrogen had been applied were frozen, such resultant leaves were crushed using a pestle and mortar.

(2) After the crushed tissues were moved to a 2.2 ml screw cap tube, 20 µl of mercaptoethanol was added to 2×CTAB of 750 µl, and the resultant, which was preheated at 56° C. by water bath, was added to such the tube mentioned above and was blended.

(3) Blending took place at room temperature (within the scope of about 15° C. through 25° C., and the same shall be applied hereinafter) for 30 minutes while being rolled.

(4) 800 µl of chloroform-isoamyl alcohol (24:1) was added for 15 to 20 minutes at room temperature while being rolled.

(5) Centrifugation took place for 15 minutes at 12,000 rpm at room temperature.

(6) After centrifugation, supernatant was collected and such supernatant was moved to a 2.2 ml screw cap tube to which 10% CTAB of 70 µl had been added in advance.

(7) CTAB precipitation buffer solution was added in 1.5 times (about 1,200 µl) the volume of solution within the tube following the process of (6) mentioned above and rolled over. At this phase, insoluble matter was precipitated.

(8) Centrifugation took place for 15 minutes at 12,000 rpm at room temperature. Thereby, insoluble matter was precipitated.

(9) After centrifugation, the supernatant was removed through decantation, and the precipitated insoluble matter was collected as a precipitate. At this time, residual liquid was sufficiently removed by conducting rollover, allowing the resultant to stand on a Kimwipe (NIPPON PAPER CRECIA Co., LTD.: registered trademark), and the like.

(10) 5 µl of TE-RNase was blended with 500 µl of High Salt TE Buffer. Such solution was added to the tube of (9) mentioned above, and the precipitate was sufficiently suspended.

(11) The tube of (10) mentioned above was incubated for more than 2 hours at 55° C. And RNA was decomposed within the precipitate.

(12) 500 µl of isopropanol were added to the tube of (11) mentioned above, and rollover and blending took place.

(13) All DNAs centrifuged and precipitated for 15 minutes at 12,000 rpm at room temperature were precipitated in the tube of (12) mentioned above.

(14) After centrifugation, supernatant was removed, 1,000 µl of 70% ethanol was gently added, and the precipitate was rinsed out.

(15) Centrifugation took place for 2 minutes at 12,000 rpm at room temperature.

(16) After 70% of ethanol had been sufficiently removed, the precipitate was dried through air drying or vacuum drying.

(17) All DNAs as the dried precipitate were suspended in 100 µl of TE. The resultant corresponded to all DNAs of *Beta vulgaris* L.

The processes following the subsequent DNA cleaving process are based on AFLP method. Herein, making use of AFLP Core Reagent Kit (Invitrogen), the following procedures were conducted in accordance with the manual included with such kit.

(B) DNA cleaving process (1) 1 µl of solution of all DNAs of *Beta vulgaris* L. prepared through the DNA extraction process, 2 µl of 5× Reaction Buffer (50 mM Tris-Hcl (pH7.5) 50 mM Mg-acetate 250 mM K-acetate) attached to the Kit mentioned above, and 0.8 µl of EcoRI/MseI (1.25 unit each) mixture included with the Kit mentioned above were added to 6.2 µl of $H_2O$ contained in a 1.5 ml tube. The resultant was sufficiently blended and DNA cleavage reaction was conducted for 2 hours at 37° C.

(2) After the DNA cleavage reaction, the reaction liquid was changed to 70° C. and kept warm for 15 minutes.

(3) After the thermal insulation treatment of (2) mentioned above, the reaction liquid was rapidly quenched at 4° C., and it was kept warm at such temperature.

Based on the processes mentioned above, all DNAs extracted from the *Beta vulgaris* L. were fragmented by EcoRI and MseI.

(C) Process for Amplifying Nucleic Acids (First Phase: Adapter Binding Process)

An adapter/ligation solution to which EcoRI adapter and MseI adapter included with the kit mentioned above and 0.4 µl of T4 DNA Ligase (10 unit/µl) included with the kit mentioned above were added was added to all solutions of 10 µl after cleavage reaction acquired through the DNA cleaving process. The resultant was sufficiently mixed. In addition, the base sequences and the number of bases for the core sequence positions of the adapter used herein are the same as those of the adapter stated in non-patent document 3.

(2) The 20 µl of reaction liquid in (1) mentioned above was incubated for 2 hours. And EcoRI adapter and/or an MseI adapter were bound to the cleaving end portion of the DNA fragments via a ligation reaction.

(3) After the ligation reaction was conducted, the reaction liquid was kept warm at 4° C.

Based on the processes mentioned above, adapter was bound to the end portion of the *Beta vulgaris* L.-derived DNA fragments.

(Second Phase: Preliminary Amplification Process)

Herein, PCR was used. Ex-Taq (TAKARA) was used for thermotolerant DNA polymerase.

(1) The reaction liquid containing products as a result of binding reaction acquired after the first phase mentioned above was diluted tenfold by TE. ("1/10 diluted template").

(2) 10.2 µl of $H_2O$ and 1/10 diluted template were inserted into a Thermal Cycler GP 384 Plate (TAKARA, and the same shall be applied hereinafter). 2 µl of 10× Buffer attached to the Ex-Taq mentioned above, 2 µl of the dNTP mix solution (dAPT, dGTP, dCTP, and dTTP, each of which corresponds to a 2.5 mM mixture) included with the Ex-Taq mentioned above, 2 µl of each of a 2.4 µM E-N primer and a 2.4 p M M-N primer included with the AFLP Core Reagent Kit, and 0.22 µl of Ex-Taq were added to the above resultant. Thereafter, sufficient blending took place.

Herein, regarding the E-N primer and the M-N primer, according to the pairs of the primers for selecting the *Aphanomyce cochlioides*-resistant plant variety used in a third phase, the following items were used.

a) In the case of using of the pairs of the primers for selecting the *Aphanomyce cochlioides*-resistant plant variety represented by SEQ ID NOs: 1 and 2 in the third phase, an E-N primer (E-G primer represented by SEQ ID: 9) and M-N primer (M-G primer represented by SEQ ID: 10) were used.

b) In the case of using of the pairs of the primers for selecting the *Aphanomyce cochlioides*-resistant plant variety represented by SEQ ID NOs: 3 and 4 in the third phase, or in the case of using of the pairs of the primers for selecting the *Aphanomyce cochlioides*-resistant plant variety represented by SEQ ID NOs: 5 and 6 in the third phase, E-N primer (E-A primer represented by SEQ ID: 11) and M-N primer (M-C primer represented by SEQ ID: 12) were used.

(3) In regards to the reaction liquid in (2) mentioned above of the present process, PCR reaction was conducted in accordance with the following program through the Thermal Cycler.

PCR reaction program: 20 cycles of a cycle of "treatment for 5 minutes at 94° C., followed by 94° C. for 30 seconds→56° C. for 1 minute→72° C. for 1 minute) were conducted. Thereafter, treatment for 10 minutes at 72° C. was performed. Finally, after cooling down at 4° C., thermal insulation was conducted.

Based on the processes mentioned above, it was possible to amplify the polynucleotides which could be the amplified polynucleotides of the target in a preliminary manner.

(Third Phase: Selection Process)

Herein, the PCR method was used. Ex-Taq (TAKARA) was used for thermotolerant DNA polymerase in the same manner as with the second phase mentioned above.

(1) The reaction liquid containing products as a result of a binding reaction acquired after the second phase mentioned above was diluted 50-fold by TE. ("1/50 diluted template").

(2) 3.6 µl of $H_2O$ and the 1/50 diluted template were added to a Thermal Cycler GP 384 Plate. 1 µl of 10× buffer included with the Ex-Taq mentioned above, 0.8 µl of dNTP mix solution (dAPT, dGTP, dCTP, and dTTP, each of which corresponds to a 2.5 mM mixture) included with the Ex-Taq mentioned above, and 1 µl of each pair of primers for selecting the *Aphanomyce cochlioides*-resistant plant variety of 2.4 µM were added to the above resultant. Thereafter, sufficient blending took place.

Herein, as pairs of primers for selecting the *Aphanomyce cochlioides*-resistant plant variety, the following pairs were used.

a) Pair of the primer for selecting the *Aphanomyce cochlioides*-resistant plant variety represented by SEQ ID: 13 based on SEQ ID: 1 and SEQ ID: 14 based on SEQ ID: 2 b) Pair of the primer for selecting the *Aphanomyce cochlioides*-resistant plant variety represented by SEQ ID: 15 based on SEQ ID: 3 and SEQ ID: 16 based on SEQ ID: 4 c) Pair of the primer for selecting the *Aphanomyce cochlioides*-resistant plant variety represented by SEQ ID: 15 based on SEQ ID: 3 and SEQ ID: 17 based on SEQ ID: 5

(3) In regards to the reaction liquid in (2) mentioned above of the present process, PCR reaction was conducted in accordance with the following program. PCR reaction program: (first amplification reaction) 13 cycles of a cycle of "treatment for 5 minutes at 94° C., followed by 94° C. for 30 seconds→65° C. for 30 seconds→72° C. for 1 minute" were conducted. At this time, 65° C. as a annealing temperature was given based on the touchdown in which lowering by 0.7° C. per cycle was conducted (second amplification reaction). Following the first amplification reaction, 20 cycles of a cycle of "94° C. for 30 seconds→65° C. for 30 seconds→72° C. for 1 minute) were conducted. Thereafter, treatment for 10 minutes at 72° C. was performed. Finally, after cooling down at 4° C., thermal insulation was conducted.

Based on the processes mentioned above, it was possible to amplify the polynucleotides which could be amplified polynucleotides of the target. 2 µl of marker dye (0.25% BPB, 0.25% XC, 1 mM EDTA (pH8.0) and 30% glycerol) was added to 10 µl of the reaction liquid that contained the acquired PCR amplified products. Such resultant corresponded to the electrophoresis sample of a detection process as below.

(D) Detection Process

Detection of amplified polynucleotides was conducted using of an acrylamide gel electrophoresis method.

(Reagent Composition)

Running gel (13% acrylamide)/sheet: 30% acrylamide (WAKO, and the same shall be applied hereinafter) and 0.8% bisacrylamide (WAKO, and the same shall be applied hereinafter) mixture 10.8 ml and 1.5M Tris-HCL (pH8.8) 6.3 ml were mixed. Thereafter, sterile water was added to the mixed resultant such that it reached 23 ml. In addition, creation of gel was conducted on ice.

Stacking gel (5% acrylamide)/sheet: 30% acrylamide and 0.8% bisacrylamide mixture 1 ml and 0.5M Tris-HCL (pH8.8) 1.6 ml were mixed. Thereafter, sterile water was added to the mixed resultant such that it reached 5.3 ml. In addition, creation of gel was conducted on the ice.

10×TBE buffer: 108 g of tris base, 55 g of boric acid, and 3.7 g of EDTA·2 Na ($2H_2O$) were mixed. Thereafter, sterile water was added to the mixed resultant such that it reached 1 L. In the case of using such item as an electrophoresis buffer, 1×TBE diluted tenfold with sterile water was used.

(Detection Method)

(1) Creation of Polyacrylamide Gel 1.5% APS and 2% TEMED were added to 23 ml of the running gel, and the resultant was stirred. Thereafter, such running gel was gently poured to a liquid quantity such that about 2.5 to 3 cm of the upper surface of the liquid were left between the glass gel plates of 18 cm×18 cm that pinched a seal tube. Subsequently, sterile water in a layer about 1 cm thick was added on top of the running gel. Such resultant was left for about 30 minutes, in order to solidify the gel. The water was removed and moisture was sufficiently eliminated by the Kimwipe. Thereafter, 1.5% APS and 2% TEMED were added to 5.3 ml of the stacking gel and the resultant was stirred. Such resultant was added on top of the solidified running gel. Next, a comb was allocated in the stacking gel without causing air bubbles to form therein, and it was left for 30 minutes to solidify the gel. Finally, polyacrylamide gel was created by removing the seal tube.

(2) Polyacrylamide Gel Electrophoresis

The aforementioned polyacrylamide gel was allocated within the electrophoresis tank (NA-1214A: NIHON EIDO). About 2.5 L of electrophoresis buffer (1×TBE) was poured into the tank. The comb was removed from the electrophoresis buffer and the well was washed with electrophoresis buffer. Thereafter, each 5 μl electrophoresis sample acquired through the third phase of the process for amplifying nucleic acid mentioned above was applied to two wells as mentioned above. 2 μl of Size Ladder Marker (100 bpDNALadder: TaKaRa) was applied to a separate well together with electrophoresis samples. Subsequently, electrophoresis was conducted for about 3 hours and 30 minutes at a voltage of 280V.

(3) Detection

After the electrophoresis mentioned above, the polyacrylamide gel was peeled off from the gel plate. Such gel was immersed in a solution in which Vistragreen (Amasham) was diluted in $1/10^{-4}$ by TBE. The resultant was vibrated loosely for about 15 minutes, and nucleic acids in the gel were dyed. Finally, ultraviolet lamp radiation of 274 nm was applied to the dyed gel and the polynucleotide banding pattern was recorded.

((Result))

The banding pattern of the polynucleotide following the gel electrophoresis via the method for selecting an *Aphanomyce cochlioides*-resistant plant variety of the present embodiment is shown in FIG. 6. In this Fig., the samples acquired through the *Aphanomyce cochlioides*-resistant plant variety of a1-a4 were applied to the 4 lanes on the left and the samples acquired through the *Aphanomyce cochlioides*-resistant plant variety of b1-b4 were applied to the 4 lanes on the right for the size marker indicated by M. I uses the first primer pair, II uses the second primer pair, and III uses the third primer pair.

As shown in FIG. 6, in regards to any of I, II, and III, polynucleotide bands were detected in a location indicated by an arrow for the 4 lanes of a1-a4. On the other hand, the same was not detected for the 4 lanes of b1-b4. As such, according to the method for selecting an *Aphanomyce cochlioides*-resistant plant variety of the first embodiment, specific polynucleotides (amplified polynucleotides) can be amplified in regards to an *Aphanomyce cochlioides*-resistant plant variety. Therefore, based on the presence or absence of such bands of amplified polynucleotides, it is easily judged whether a targeted strain for examination correspond to an *Aphanomyce cochlioides*-resistant plant variety or an *Aphanomyce cochlioides*-susceptible plant variety.

What is claimed is:

1. A method for selecting an *Aphanomyce cochlioides*-resistant plant variety comprising the steps of:
   (i) extracting DNA from tissues of a plant from the genus *Beta*; cleaving the extracted DNA with a restriction enzyme;
   (ii) amplifying nucleic acids as pairs of primer for selecting an *Aphanomyce cochlioides*-resistant plant variety, which is composed of the base sequences of SEQ ID NO: 1 and SEQ ID NO: 2; and
   (iii) detecting polynucleotides that contain the base sequence of SEQ ID NO: 6 from among the nucleic acids amplified in step (ii) to select the *Aphanomyces cochlioides*-resistant plant variety.

2. A method for selecting an *Aphanomyce cochlioides*-resistant plant variety comprising the steps of:
   (i) extracting DNA from tissues of a plant from the genus *Beta* and cleaving the extracted DNA with a restriction enzyme;
   (ii) amplifying nucleic acids as pairs of primer for selecting an *Aphanomyce cochlioides*-resistant plant variety, which is composed of the base sequences of SEQ ID NO: 3 and SEQ ID NO: 4; and
   (iii) detecting polynucleotides that contain the base sequence of SEQ ID NO: 7 from among the nucleic acids amplified in step (ii) to select the *Aphanomyces cochlioides*-resistant plant variety.

3. A method for selecting an *Aphanomyce cochlioides*-resistant plant variety comprising the steps of:
   (i) extracting DNA from tissues of a plant from the genus *Beta*; and cleaving the extracted DNA with a restriction enzyme;
   (ii) amplifying nucleic acids as pairs of primers for selecting an *Aphanomyce cochlioides*-resistant plant variety, which is composed of the base sequences of SEQ ID NO: 3 and SEQ ID NO: 5; and
   (iii) detecting polynucleotides that contain the base sequence of SEQ ID NO: 8 from among the nucleic acids amplified in step (ii) to select the *Aphanomyces cochlioides*-resistant plant variety.

4. The method for selecting an *aphanomyces cochlioides*-resistant plant variety according to claim 1, in which the plant of the *Beta* genus is *Beta vulgaris* L.

5. A method for producing seeds or progeny of the genus *Beta* having resistance against *Aphanomyce cochlioides* comprising the steps of:
   (i) extracting DNA from tissues of a plant from the genus *Beta*; and cleaving the extracted DNA with a restriction enzyme;
   (ii) amplifying nucleic acids as pairs of primer for selecting an *Aphanomyce Aphanomyces cochlioides*-resistant plant variety, which is composed of the base sequences of SEQ ID NO: 1 and SEQ ID NO:2;
   (iii) detecting polynucleotides that contain the base sequence of SEQ ID NO: 6 from among the nucleic acids amplified in step (ii) to select the *Aphanomyce cochlioides*-resistant plant variety;
   (iv) acquiring a tissue sample from the root portion of the selected *Aphanomyce cochlioides*-resistant plant variety;
   (v) dedifferentiating the tissue sample;
   (vi) inducing callus formation from the dedifferentiated tissue sample; and
   (vii) cultivating the callus to obtain seeds or progeny having resistance against *Aphanomyce cochliodes*.

6. The method for selecting an *aphanomyces cochlioides*-resistant plant variety according to claim 2, in which the plant of the *Beta* genus is *Beta vulgaris* L.

7. The method for selecting an *aphanomyces cochlioides*-resistant plant variety according to claim 3, in which the plant of the *Beta* genus is *Beta vulgaris* L.

8. A method for producing seeds or progeny of the genus *Beta* having resistance against *Aphanomyce cochlioides* comprising the steps of:
   (i) extracting DNA from tissues of a plant from the genus *Beta*; and cleaving the extracted DNA with a restriction enzyme;
   (ii) amplifying nucleic acids as pairs of primer for selecting an *Aphanomyce Aphanomyces cochlioides*-resistant plant variety, which is composed of the base sequences of SEQ ID NO: 3 and SEQ ID NO: 4;
   (iii) detecting polynucleotides that contain the base sequence of SEQ ID NO: 7 from among the nucleic acids amplified in step (ii) to select the *Aphanomyce cochlioides*-resistant plant variety;
   (iv) acquiring a tissue sample from the root portion of the selected *Aphanomyce cochlioides*-resistant plant variety;
   (v) dedifferentiating the tissue sample;
   (vi) inducing callus formation from the dedifferentiated tissue sample; and
   (vii) cultivating the callus to obtain seeds or progeny having resistance against *Aphanomyce cochliodes*.

9. A method for producing seeds or progeny of the genus *Beta* having resistance against *Aphanomyce cochlioides* comprising the steps of:
   (i) extracting DNA from tissues of a plant from the genus *Beta* and cleaving the extracted DNA with a restriction enzyme;

(ii) amplifying nucleic acids as pairs of primer for selecting an *Aphanomyce cochlioides*-resistant plant variety, which is composed of the base sequences of SEQ ID NO: 3 and SEQ ID NO: 5;
(iii) detecting polynucleotides that contain the base sequence of SEQ ID NO: 8 from among the nucleic acids amplified in step (ii) to select the *Aphanomyce cochlioides*-resistant plant variety;
(iv) acquiring a tissue sample from the root portion of the selected *Aphanomyce cochlioides*-resistant plant variety;
(v) dedifferentiating the tissue sample;
(vi) inducing callus formation from the dedifferentiated tissue sample; and
(vii) cultivating the callus to obtain seeds or progeny having resistance against *Aphanomyce cochliodes*.

* * * * *